(12) United States Patent
Sethofer et al.

(10) Patent No.: US 7,378,415 B2
(45) Date of Patent: May 27, 2008

(54) BENZOXAZINE AND QUINOXALINE DERIVATIVES AND USES THEREOF

(75) Inventors: Steven Sethofer, Campbell, CA (US); Li Zhang, San Carlos, CA (US); Shu-Hai Zhao, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 217 days.

(21) Appl. No.: 11/241,632

(22) Filed: Sep. 30, 2005

(65) Prior Publication Data

US 2006/0106012 A1    May 18, 2006

Related U.S. Application Data

(60) Provisional application No. 60/630,608, filed on Nov. 24, 2004, provisional application No. 60/614,705, filed on Sep. 30, 2004, provisional application No. 60/707,798, filed on Aug. 12, 2005.

(51) Int. Cl.
  *C07D 265/36* (2006.01)
  *A61K 31/538* (2006.01)
(52) U.S. Cl. .................. 514/230.5; 544/105
(58) Field of Classification Search ............ 544/105; 514/230.5
  See application file for complete search history.

(56) References Cited

U.S. PATENT DOCUMENTS

| 5,321,025 | A | 6/1994 | Bruneau |
| 5,475,009 | A | 12/1995 | Chernesky et al. |
| 5,691,362 | A | 11/1997 | McCormick et al. |
| 6,867,204 | B2 | 3/2005 | Berger et al. |

FOREIGN PATENT DOCUMENTS

| EP | 0 432 893 A2 | 6/1991 |
| EP | 0 570 112 A1 | 11/1993 |
| EP | 0 462 813 B1 | 10/1995 |
| EP | 0 462 830 B1 | 10/1995 |
| EP | 0 407 137 B1 | 5/1996 |
| JP | 2000 327663 | 11/2000 |
| WO | WO 92/16524 A1 | 10/1992 |
| WO | WO 94/05281 A1 | 3/1994 |
| WO | WO 94/26739 A1 | 11/1994 |
| WO | WO 95/30668 A1 | 11/1995 |
| WO | WO 98/00412 A1 | 1/1998 |
| WO | WO 98/50372 A1 | 11/1998 |
| WO | WO 01/57003 A1 | 8/2001 |
| WO | WO 02/072049 A1 | 9/2002 |
| WO | WO 02/085868 A1 | 10/2002 |

OTHER PUBLICATIONS

Rusell MG and Dias R. (Curr. Top. Med. Chem, Jun. 2002; 2(6):643-54).*

* cited by examiner

*Primary Examiner*—Kahsay T Habte
(74) *Attorney, Agent, or Firm*—Robert C. Hall

(57) ABSTRACT

Compounds of the formula I:

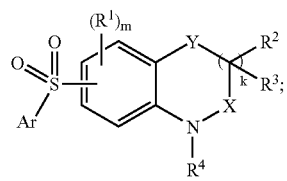

or a pharmaceutically acceptable salt, solvate or prodrug thereof, wherein k, m, n, p, q, X, Y, Z, Ar, $R^1$, $R^2$, $R^3$ and $R^4$ are as defined herein. Also provided are methods for preparing, compositions comprising, and methods for using compounds of formula I.

17 Claims, No Drawings

BENZOXAZINE AND QUINOXALINE DERIVATIVES AND USES THEREOF

CROSS-REFERENCE

This application claims the benefit of priority of U.S. Provisional Patent Application Ser. No. 60/630,608 filed Nov. 24 2004, U.S. Provisional Patent Application Ser. No. 60/614,705 filed Sep. 30, 2004, and U.S. Provisional Patent Application Ser. No. 60/707,798 filed Aug. 12, 2005, the disclosures of which are incorporated herein by reference in their entirety.

FIELD OF THE INVENTION

This invention relates to substituted benzoxazine and quinoxaline compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ED Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

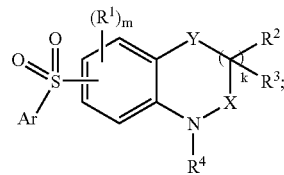

or pharmaceutically acceptable salts thereof, wherein:

X is —$CH_2$— or C=O;

Y is O or $NR^a$ wherein $R^a$ is hydrogen or alkyl;

k is 1 or 2;

m is from 0 to 3;

each $R^1$ is independently halo, alkyl, haloalkyl, heteroalkyl, alkoxy, cyano, —$S(O)_q$—$R^b$, —C(=O)—$NR^cR^d$, —$SO_2$—$NR^cR^d$, —$N(R^e)$—C(=O)—$R^f$, or —C(=O)—$R^f$, where q is from 0 to 2, $R^b$, $R^c$, $R^d$ and $R^e$ each independently is hydrogen or alkyl, and $R^f$ is hydrogen, alkyl, alkoxy or hydroxy;

$R^2$ and $R^3$ each independently is hydrogen or alkyl, or $R^2$ and $R^3$ together with the carbon atom to which they are attached may form a carbocyclic ring of four to six members;

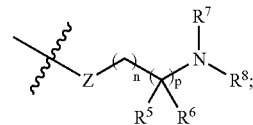

$R^4$ is a group of the formula

Z is a bond, —(C=O)—, or —$SO_2$—;

n is from 0 to 4;

p is 0 or 1;

$R^5$ and $R^6$ each independently is hydrogen or alkyl; and $R^7$ and $R^8$ each independently is hydrogen, alkyl, —C=$NR^g$)—$NR^hR^i$, or —$(CH_2)_2$—$NR^hR^i$ wherein $R^g$, $R^h$ and $R^i$ each independently is hydrogen or alkyl, or $R^7$ and $R^8$ together with the nitrogen to which they are attached may form a four, five or six-membered ring that optionally includes an additional heteroatom selected from O, N and S, or one of $R^5$ and $R^6$ together with one of $R^7$ and $R^8$ together with the atoms to which they are attached may form a ring of four to six members.

The invention also provides methods for preparing the aforementioned compounds. The subject methods may comprise, in certain embodiments:

reacting a compound of the formula d

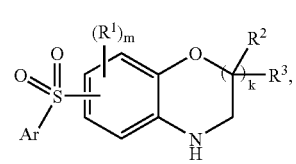

wherein k, m, Ar, $R^1$, $R^2$ and $R^3$ are as defined herein, with an alkylating agent of formula e

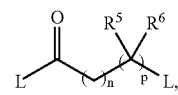

wherein n, p, L, $R^5$ and $R^6$ are as defined herein, to provide a compound of formula f

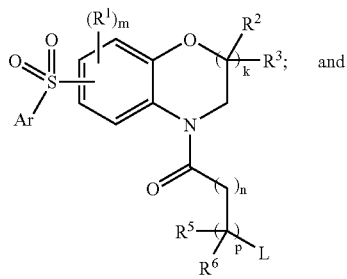

reacting the compound of formula f with an amine HNR$^7$R$^8$ wherein R$^7$ and R$^8$ are as defined herein, to yield a compound of formula g

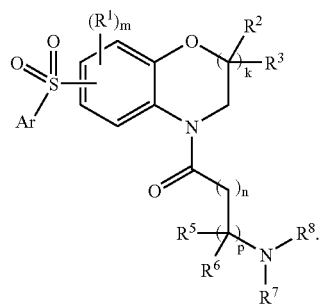

The method may further comprise reducing the compound g to provide a compound of formula h

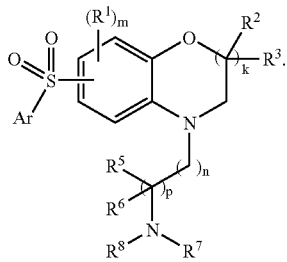

The invention further provides compositions comprising, and methods for using the aforementioned compounds.

DETAILED DESCRIPTION OF THE INVENTION

The invention provides substituted quinolinone compounds, associated compositions, methods for use as therapeutic agents, and methods of preparation thereof. In specific embodiments the invention provides piperazinyl-substituted quinolinone compounds and associated pharmaceutical compositions, and methods for using the same in the treatment of central nervous system (CNS) diseases and gastrointestinal tract disorders.

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$-$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH═CH—), 2,2-dimethylethenylene, propenylene, 2-methylpropenylene, butenylene, pentenylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benizoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —R$^a$R$^b$ where R$^a$ is an alkylene group and R$^b$ is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Optionally substituted", when used in association with "aryl", "arylene", phenyl", "phenylene", "heteroaryl", "heteroarylene or "heterocyclyl", means an aryl, arylene, phenyl, phenylene, heteroaryl, heteroarylene, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. For convenience, the IUPAC numbering of the positions of representative benzoxazine compounds described herein is shown by the formula:

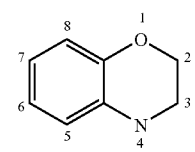

Chemical structures shown herein were prepared using ISIS® version 2.2. Any open valency appearing on a carbon, oxygen or nitrogen atom in the structures herein indicates the presence of a hydrogen. Where a chiral center is present in a structure but no specific enantiomer is shown, the structure encompasses both enantiomers associated with the chiral center.

Compounds of the Invention

The invention provides compounds of the formula I:

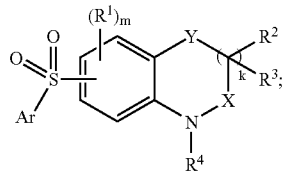

or pharmaceutically acceptable salts thereof, wherein:

X is —CH$_2$— or C=O;

Y is O or NR$^a$ wherein R$^a$ is hydrogen or alkyl;

k is 1 or 2;

m is from 0 to 3;

each R$^1$ is independently halo, alkyl, haloalkyl, heteroalkyl, alkoxy, cyano, —S(O)$_q$—R$_b$, —C(=O)—NR$^c$R$^d$, —SO$_2$—NR$^c$R$^d$, —N(R$^e$)—C(=O)—R$^f$, or —C(=O)—R$^f$, where q is from 0 to 2, R$^b$, R$^c$, R$^d$ and R$^e$ each independently is hydrogen or alkyl, and R$^f$ is hydrogen, alkyl, alkoxy or hydroxy;

R$^2$ and R$^3$ each independently is hydrogen or alkyl, or R$^2$ and R$^3$ together with the carbon atom to which they are attached may form a carbocyclic ring of four to six members;

R$^4$ is a group of formula

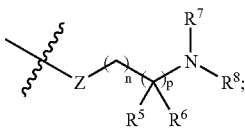

Z is a bond, —(C=O)—, or —SO$_2$—;

n is from 0 to 4;

p is 0 or 1;

R$^5$ and R$^6$ each independently is hydrogen or alkyl; and

R$^7$ and R$^8$ each independently is hydrogen, alkyl, —C=NR$^g$)—NR$^h$R$^i$, or —(CH$_2$)$_2$—NR$^h$R$^i$ wherein R$^g$, R$^h$ and R$^i$ each independently is hydrogen or alkyl, or R$^7$ and R$^8$ together with the nitrogen to which they are attached may form a four, five or six-membered ring that optionally includes an additional heteroatom selected from O, N and S, or one of R$^5$ and R$^6$ together with one of R$^7$ and R$^8$ together with the atoms to which they are attached may form a ring of four to six members.

It should be understood that the scope of this invention encompasses not only the various isomers which may exist but also the various mixture of isomers which may be formed. Furthermore, the scope of the present invention also encompasses solvates and salts of compounds of formula I.

In many embodiments of formula I, k is 1. In certain embodiments of formula I, X is —CH$_2$—. In other embodiments of formula I, X is C=O. Preferably X is —CH$_2$—. In certain embodiments of formula I, Y may be O, while in other embodiments Y may be N. Preferably Y is O. In many embodiments of formula I, Z is —(C=O)— or a bond.

The compounds of the invention may, in certain embodiments, be of formula IIa or IIb:

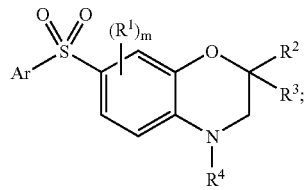

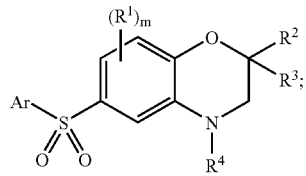

wherein m, R$^1$, R$^2$, R$^3$ and R$^4$ are as defined herein.

In certain embodiments of formulas I, IIa and IIb, R$^2$ and R$^3$ are both hydrogen, while in some embodiments R$^2$ and R$^3$ are both alkyl, and in other embodiments one of R$^2$ and R$^3$ is hydrogen and the other is alkyl. In many embodiments of formulas I, IIa and IIb Ar is aryl such as optionally substituted phenyl or optionally substituted naphthyl, and more specifically optionally substituted phenyl. In embodiments where Ar is heteroary, Ar may be thienyl, pyridyl, pyrimidinyl, quinolinyl or isoquinolinyl, each optionally substituted.

In certain embodiments of formulas I, IIa and IIb, Z is —C(=O)—. In such embodiments, n and p may both be 0. In specific embodiments, R$^7$ may be hydrogen while R$^8$ is —(C=NR$^d$)—NR$^e$R$^f$. In still other embodiments R$^7$ may be hydrogen while R$^8$ is —(CH$_2$)$_2$—NR$^g$R$^h$.

In some embodiments of formulas I, IIa and IIb where Z is —C(=O)—, n is 0 and p is 1. In such embodiments R$^5$ and R$^6$ may both be hydrogen. In other embodiments R$^7$ and R$^8$ may each independently is hydrogen or alkyl. In still other embodiments one of R$^5$ and R$^6$ and one of R$^7$ and R$^8$ together with the atoms to which they are attached form a ring of four to six members.

In still other embodiments of formulas I, IIa and IIb where Z is —C(=O)—, n is 1 and p is 1. In such embodiments R$^5$ and R$^6$ may both be hydrogen. In other embodiments R$^7$ and R$^8$ may each independently is hydrogen or alkyl. In still other embodiments one of R$^5$ and R$^6$ and one of R$^7$ and R$^8$ together with the atoms to which they are attached form a ring of four to six members. In specific embodiments one of R$^5$ and R$^6$ and of R$^7$ and R$^8$ together with the atoms to which they are attached form an imidazolinyl ring.

In certain embodiments of formulas I, IIa and IIb, Z is a bond. In such embodiments, n may be 0, while p is 1. In specific embodiments one of R$^5$ and R$^6$ and of R$^7$ and R$^8$ together with the atoms to which they are attached form a ring of four to six members.

In other embodiments of formulas I, IIa and IIb where Z is a bond, n is 1 and p is 1. In such embodiments R$^5$ and R$^6$ may both be hydrogen. In other embodiments R$^7$ and R$^8$ may each independently be hydrogen or alkyl. In still other embodiments one of R$^5$ and R$^6$ and one of R$^7$ and R$^8$ together with the atoms to which they are attached form a ring of four to six members. In specific embodiments one of R$^5$ and R$^6$ and of R$^7$ and R$^8$ together with the atoms to which they are attached form an imidazolinyl ring.

In still other embodiments of formulas I, IIa and IIb where Z is a bond, n is 2 and p is 1. In such embodiments $R^5$ and $R^6$ may both be hydrogen. In other embodiments $R^7$ and $R^8$ may each independently be hydrogen or alkyl.

In yet other embodiments of formulas I, IIa and IIb where Z is a bond, n is 3 and p is 1. In such embodiments $R^5$ and $R^6$ may both be hydrogen, while in other embodiments $R^7$ and $R^8$ may each independently be hydrogen or alkyl.

In certain embodiments of formulas I, IIa and IIb, $R^4$ may be: aminoalkyl; alkylaminoalkyl; dialkylaminoalkyl; imidazolinylalkyl; imidazolylalkyl; piperidinyl; pyrrolidinyl; azetidinyl; pyridinyl; piperidinylalkyl; pyrrolidinylalkyl; azetidinylalkyl; aminoalkylcarbonyl; alkylaminoalkylcarbonyl; dialkylaminoalkylcarbonyl; imidazolinylalkylcarbonyl; imidazolylalkylcarbonyl; aminoalkylaminocarbonyl; guanidinylcarbonyl; piperidinylcarbonyl; pyrrolidinylcarbonyl; azetidinylcarbonyl; pyridinylcarbonyl; piperidinylalkylcarbonyl; pyrrolidinylalkylcarbonyl; or azetidinylalkylcarbonyl.

In certain embodiments of formulas I, IIa and IIb, $R^4$ may be: aminoalkyl; alkylaminoalkyl; dialkylaminoalkyl; imidazolinylalkyl; imidzaolylalkyl; piperidinyl; pyrrolidinyl; pyridinyl; azetidinylalkyl; aminoalkylcarbonyl; alkylaminoalkylcarbonyl; dialkylaminoalkylcarbonyl; imidazolinylalkylcarbonyl; aminoalkylaminocarbonyl; guanidinylcarbonyl; piperidinylcarbonyl; pyrrolidinylcarbonyl; or azetidinylcarbonyl.

In certain embodiments of formulas I, IIa and IIb, $R^4$ may be: 2-dimethylaminoethyl; 3-dimethylaminopropyl; 4-dimethylaminobutyl; 2-aminoethyl; 3-methylaminopropyl; imidazolin-2-ylmethyl; piperidin-4-yl; 2-imidazol-1-yl-ethyl; azetidin-3-ylmethyl; pyrrolidin-3-yl; pyridin-4-yl; imidazolin-2-ylmethylcarbonyl; guanidinylcarbonyl; 2-aminoethylaminocarbonyl; 2-dimethylaminoethylcarbonyl; 2-methylaminoethylcarbonyl; methylaminomethylcarbonyl; dimethylaminomethylcarbonyl; 2-aminoethylaminocarbonyl; azetidin-3-yl-carbonyl; pyrroldin-3-yl-carbonyl; piperidin-3-yl-carbonyl; or piperidin-4-yl-carbonyl.

In certain embodiments of formulas I, IIa and IIb, $R^4$ may be:

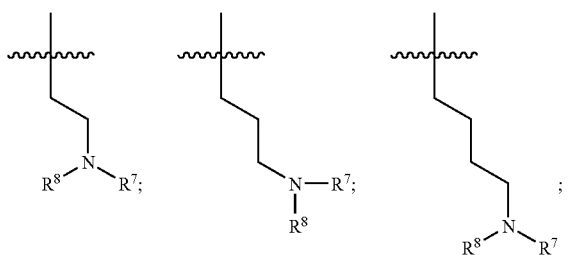

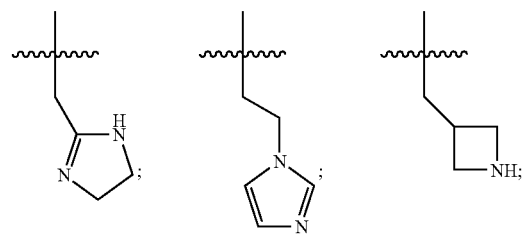

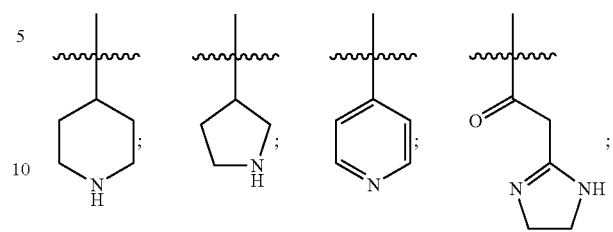

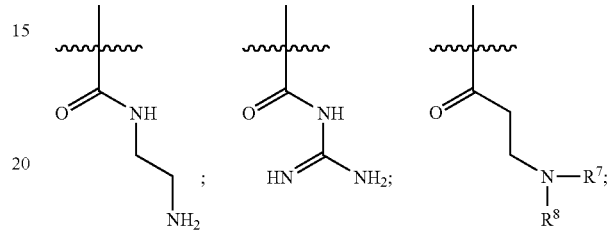

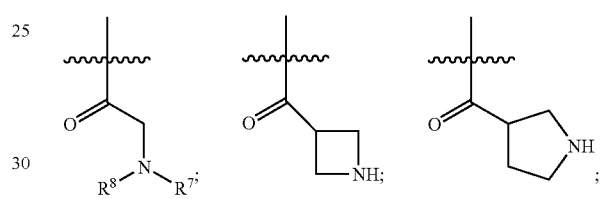

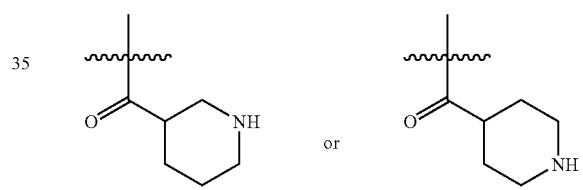

In certain embodiments of formulas I, IIa and IIb, $R^4$ is:

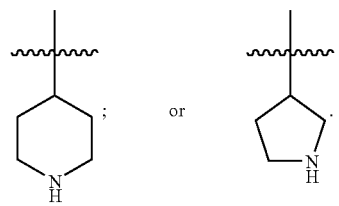

In specific embodiments of formulas I, IIa and IIb, $R^4$ is:

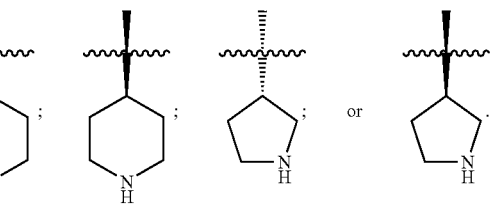

In certain embodiments, the compounds of the invention may be of formula IIIa or IIIb:

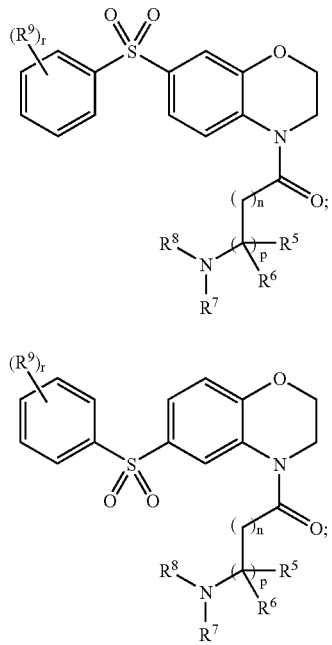

IIIa

IIIb wherein:

r is from 0 to 4;

each $R^9$ independently is halo, alkyl, haloalkyl, heteroalkyl, alkoxy, cyano, —S(O)$_s$—$R^j$, —C(=O)—NR$^k$R$^m$, —SO$_2$—NR$^k$R$^m$, —N(R$^n$)—C(=O)—R$^p$, or —C(=O)—R$^p$, where s is from 0 to 2, R$^j$, R$^k$, R$^m$ and R$^n$ each independently is hydrogen or alkyl, and R$^p$ is hydrogen, alkyl, alkoxy or hydroxy; and n, p, $R^5$, $R^6$, $R^7$ and $R^8$ are as defined herein.

In certain embodiments of formulas IIIa and IIIb, r is 0 or 1 and $R^9$ is halo, alkyl, alkoxy or haloalkyl.

In certain embodiments of of formulas IIIa and IIIb, n and p may both be 0. In such embodiments, $R^7$ may be hydrogen while $R^8$ is —(C=NR$^d$)—NR$^e$R$^f$. In other embodiments $R^7$ may be hydrogen while $R^8$ is —(CH$_2$)$_2$—NR$^g$R$^h$.

In some embodiments of formulas IIIa and IIIb, n is 0 and p is 1. In such embodiments $R^5$ and $R^6$ may both be hydrogen. In other embodiments $R^7$ and $R^8$ may each independently be hydrogen or alkyl. In still other embodiments one of $R^5$ and $R^6$ and one of $R^7$ and $R^8$ together with the atoms to which they are attached form a ring of four to six members.

In still other embodiments of formulas IIIa and IIIb, n is 1 and p is 1. In such embodiments $R^5$ and $R^6$ may both be hydrogen. In other embodiments $R^7$ and $R^8$ may each independently be hydrogen or alkyl. In still other embodiments one of $R^5$ and $R^6$ and one of $R^7$ and $R^8$ together with the atoms to which they are attached form a ring of four to six members. In specific embodiments one of $R^5$ and $R^6$ and of $R^7$ and $R^8$ together with the atoms to which they are attached form an imidazolinyl ring.

In certain embodiments, the compounds of the invention may be of formula IVa or IVb:

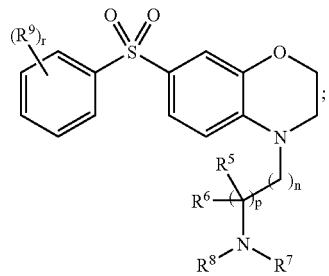

IVa

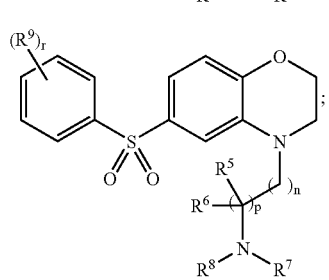

IVb wherein n, p, r, $R^5$, $R^6$, $R^7$, $R^8$ and $R^9$ are as defined herein.

In certain embodiments of formulas IVa and IVb, r is 0 or 1 and $R^9$ is halo, alkyl, alkoxy or haloalkyl.

In certain embodiments of of formulas IVa and IVb, n may be 0, while p is 1. In such embodiments one of $R^5$ and $R^6$ and of $R^7$ and $R^8$ together with the atoms to which they are attached form a ring of four to six members.

In other embodiments of formulas IVa and IVb, n is 1 and p is 1. In such embodiments $R^5$ and $R^6$ may both be hydrogen. In other embodiments $R^7$ and $R^8$ may each independently be hydrogen or alkyl. In still other embodiments one of $R^5$ and $R^6$ and one of $R^7$ and $R^8$ together with the atoms to which they are attached form a ring of four to six members. In specific embodiments one of $R^5$ and $R^6$ and of $R^7$ and $R^8$ together with the atoms to which they are attached form an imidazolinyl ring.

In still other embodiments of formulas IVa and IVb, n is 2 and p is 1. In such embodiments $R^5$ and $R^6$ may both be hydrogen. In other embodiments $R^7$ and $R^8$ may each independently be hydrogen or alkyl.

In yet other embodiments of formulas IVa and IVb, n is 3 and p is 1. In such embodiments $R^5$ and $R^6$ may both be hydrogen, while in other embodiments $R^7$ and $R^8$ may each independently be hydrogen or alkyl.

In certain embodiments, the compounds of the invention may be of formula Va or Vb:

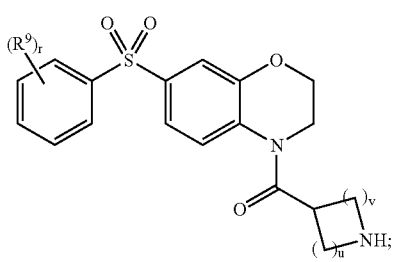

Va

-continued

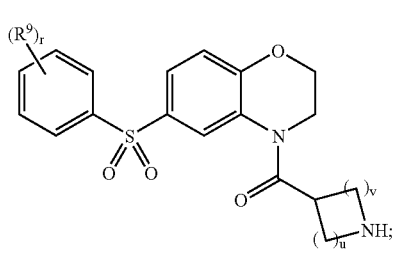
Vb wherein:
u and v each independently is 1 or 2; and
r and R⁹ are as defined herein.

In certain embodiments of formulas Va and Vb, r is 0 or 1 and R⁹ is halo, alkyl, alkoxy or haloalkyl.

In certain embodiments of formulas Va and Vb, u and v are 1. In other embodiments, one of u and v is 1 while the other is 2. In still other embodiments u and v are both 2.

In certain embodiments, the compounds of the invention may be of formula VIa or VIb:

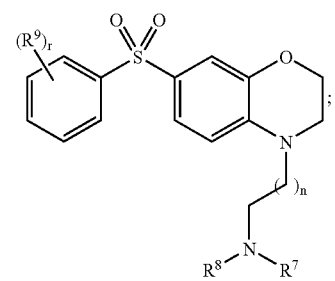
VIa

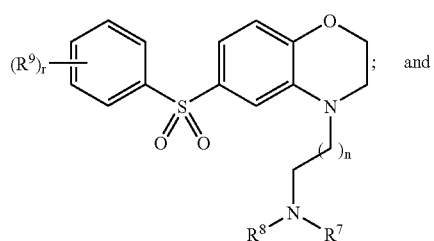
VIb; and wherein n, r, R⁷, R⁸ and R⁹ are as defined herein.

In certain embodiments of formulas VIa and VIb, r is 0 or 1 and R⁹ is halo, alkyl, alkoxy or haloalkyl.

In certain embodiments of formulas VIa and VIb, n is 1. In such embodiments R⁵ and R⁶ may both be hydrogen. In other embodiments R⁷ and R⁸ may each independently be hydrogen or alkyl.

In other embodiments of formulas VIa and VIb, n is 2. In such embodiments R⁵ and R⁶ may both be hydrogen. In other embodiments R⁷ and R⁸ may each independently be hydrogen or alkyl.

In certain embodiments of formulas VIa and VIb, n is 3. In such embodiments R⁵ and R⁶ may both be hydrogen. In other embodiments R⁷ and R⁸ may each independently be hydrogen or alkyl.

In certain embodiments, the compounds of the invention may be of formula VIIa or VIIb:

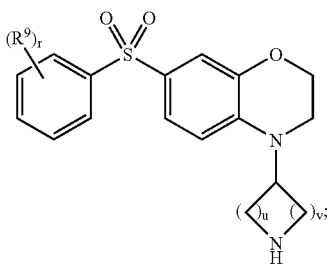
VIIa

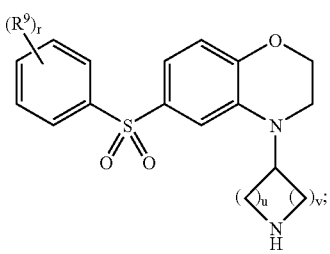
VIIb wherein u, v, r and R⁹ are as defined herein.

In certain embodiments, the compounds of the invention may be of formula VIIai, VIaii, VIIbi or VIbii:

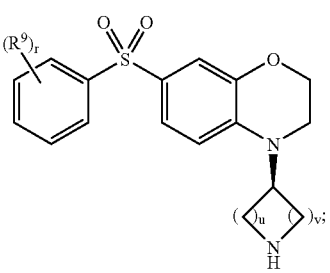
VIIai

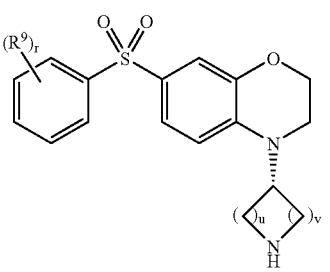
VIIaii

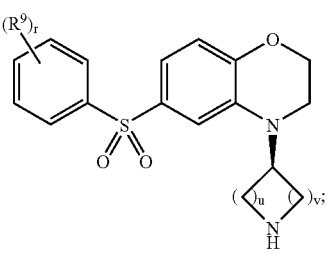
VIIbi

-continued

VIIbii

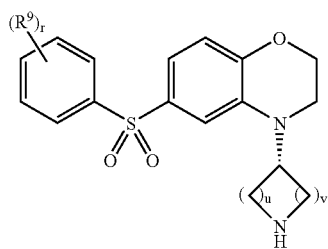

wherein u, v, r and R⁹ are as defined herein.

In certain embodiments of formulas VIIa, VIIb, VIIai, VIIii, VIIbi, VIIbii, r is 0 or 1 and $R^9$ is halo, alkyl, alkoxy or haloalkyl.

In certain embodiments of formulas VIIa, VIIb, VIIai, VIIii, VIIbi, VIIbii, u and v are 1. In other embodiments, one of u and v is 1 while the other is 2. In still other embodiments u and v are both 2.

Where any of $R^1$, $R^2$, $R^3$, $R^4$, $R^5$, $R^6$, $R^7$, $R^8$ and $R^9$ herein are alkyl or contain an moiety, such alkyl is preferably lower alkyl, i.e. $C_1$-$C_6$alkyl, and more preferably $C_1$-$C_4$alkyl.

Representative compounds in accordance with the invention are shown in Table 1 together with melting point or mass spectrum M+H, and the experimental examples (described below) associated with each compound. Melting points shown are the the corresponding hydrochloride salts unless indicated otherwise.

TABLE 1

| # | Structure | Name | MP° C./ M + H | Example |
|---|---|---|---|---|
| 1 | 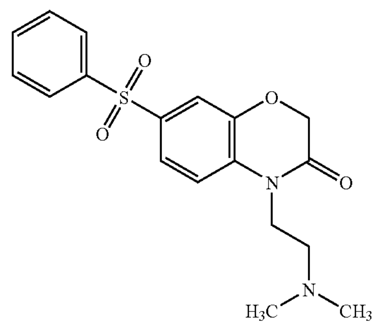 | 7-Benzenesulfonyl-4-(2-dimethylamino-ethyl)-4H-benzo[1,4]oxazin-3-one | 232.9–235.3° C. | 1 |
| 2 | 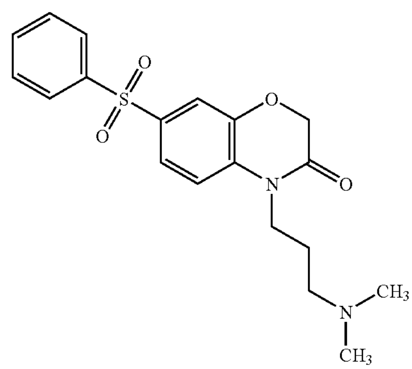 | 7-Benzenesulfonyl-4-(3-dimethylamino-propyl)-4H-benzo[1,4]oxazin-3-one | 194.0–196.1° C. | 1 |
| 3 | 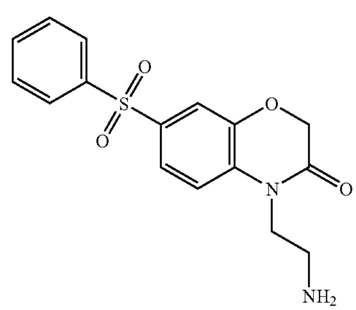 | 4-(2-Amino-ethyl)-7-benzenesulfonyl-4H-benzo[1,4]oxazin-3-one | 206.9–209.1° C. | 3 |

TABLE 1-continued

| # | Structure | Name | MP° C./ M + H | Example |
|---|-----------|------|---------------|---------|
| 4 | 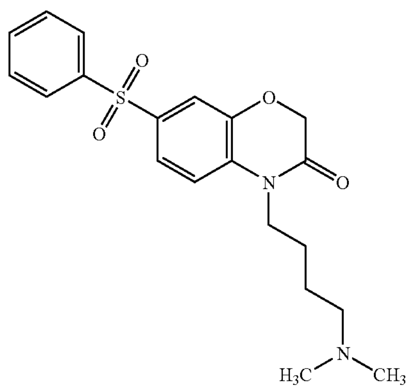 | 7-Benzenesulfonyl-4-(4-dimethylamino-butyl)-4H-benzo[1,4]oxazin-3-one | 179.0–180.0° C. | 1 |
| 5 | 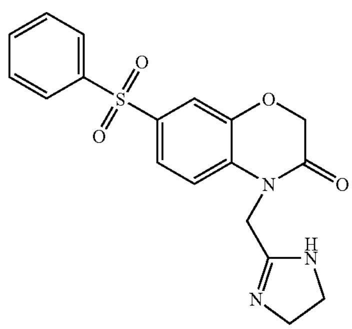 | 7-Benzenesulfonyl-4-(4,5-dihydro-1H-imidazol-2-ylmethyl)-4H-benzo[1,4]oxazin-3-one | 113.7–116.0° C. | 2 |
| 6 | 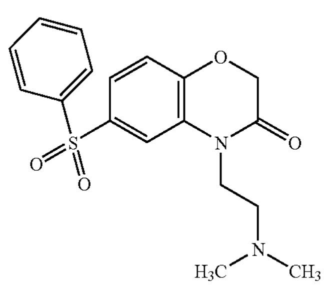 | 6-Benzenesulfonyl-4-(2-dimethylamino-ethyl)-4H-benzo[1,4]oxazin-3-one | 204.0–206.9° C. | 1 |
| 7 | 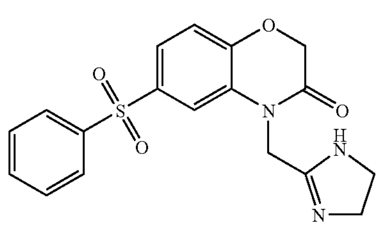 | 6-Benzenesulfonyl-4-(4,5-dihydro-1H-imidazol-2-ylmethyl)-4H-benzo[1,4]oxazin-3-one | 250.0–257.0° C. | 2 |
| 8 | 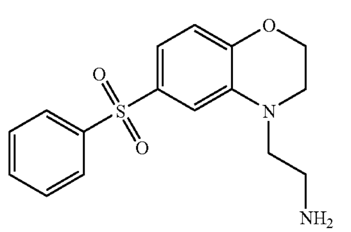 | 2-(6-Benzenesulfonyl-2,3-dihydro-benzo[1,4]oxazin-4-yl)-ethylamine | 242.9–245.9° C. | 5 |

TABLE 1-continued

| # | Structure | Name | MP° C./ M + H | Example |
|---|---|---|---|---|
| 9 | 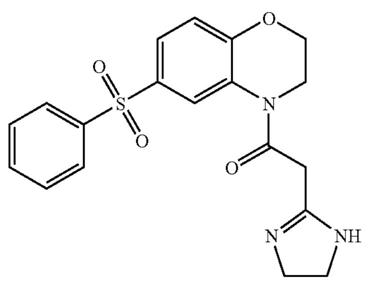 | 1-(6-Benzenesulfonyl-2,3-dihydro-benzo[1,4]oxazin-4-yl)-2-(4,5-dihydro-1H-imidazol-2-yl)-ethanone | 202.3–203.6° C. | 6 |
| 10 | 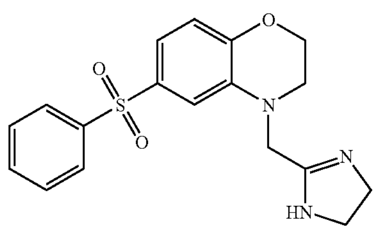 | 6-Benzenesulfonyl-4-(4,5-dihydro-1H-imidazol-2-ylmethyl)-3,4-dihydro-2H-benzo[1,4]oxazine | 114.0–116.1° C. | 2 |
| 11 | 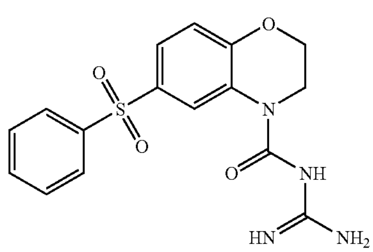 | 6-Benzenesulfonyl-2,3-dihydro-benzo[1,4]oxazine-4-carbonyl)-guanidine | 148.5–151.6° C. | 7 |
| 12 | 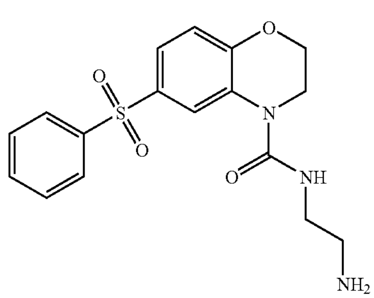 | 6-Benzenesulfonyl-2,3-dihydro-benzo[1,4]oxazine-4-carboxylic acid (2-amino-ethyl)-amide | 172.4–181.3° C. | 8 |
| 13 | 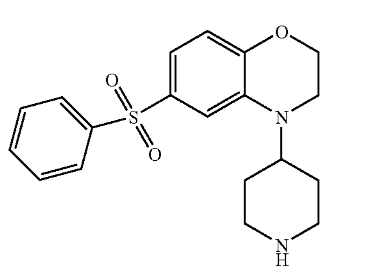 | 6-Benzenesulfonyl-4-piperidin-4-yl-3,4-dihydro-2H-benzo[1,4]oxazine | 147.0–149.8° C. | 11 |

TABLE 1-continued

| # | Structure | Name | MP° C./ M + H | Example |
|---|---|---|---|---|
| 14 | 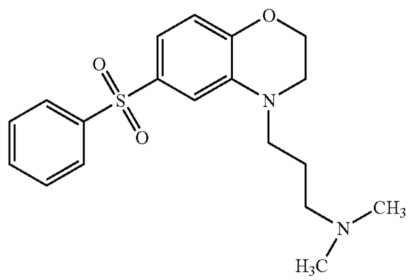 | 1-(6-Benzenesulfonyl-2,3-dihydro-benzo[1,4]oxazin-4-yl)-3-dimethylamino-propan-1-one | 81.0–82.0° C. | 9 |
| 15 | 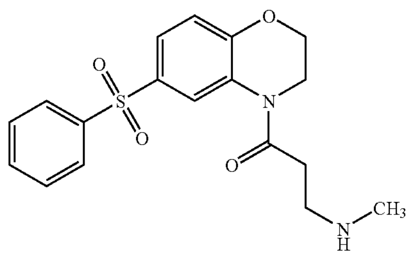 | 1-(6-Benzenesulfonyl-2,3-dihydro-benzo[1,4]oxazin-4-yl)-3-methylamino-propan-1-one | 208.3–214.7° C. | 9 |
| 16 | 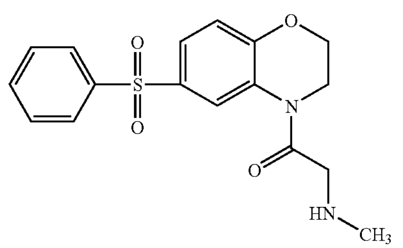 | 1-(6-Benzenesulfonyl-2,3-dihydro-benzo[1,4]oxazin-4-yl)-2-methylamino-ethanone | 233.0–235.5° C. | 9 |
| 17 | 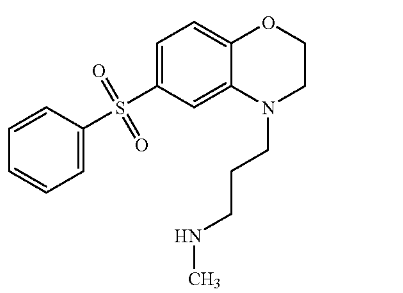 | [3-(6-Benzenesulfonyl-2,3-dihydro-benzo[1,4]oxazin-4-yl)-propyl]-methyl-amine | 235.1–236.9° C. | 9 |
| 18 | 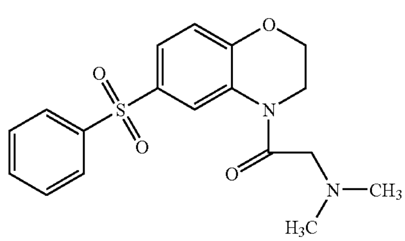 | 1-(6-Benzenesulfonyl-2,3-dihydro-benzo[1,4]oxazin-4-yl)-2-dimethylamino-ethanone | 199.0–203.0° C. | 9 |

TABLE 1-continued

| # | Structure | Name | MP° C./ M + H | Example |
|---|---|---|---|---|
| 19 | 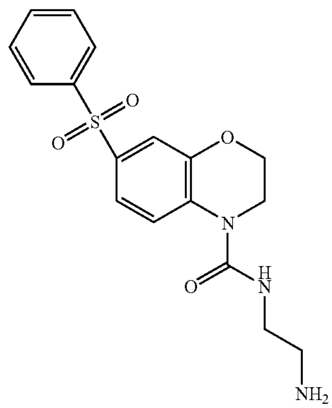 | 7-Benzenesulfonyl-2,3-dihydro-benzo[1,4]oxazine-4-carboxylic acid (2-amino-ethyl)-amide | 220.9–221.3° C. | 8 |
| 20 | 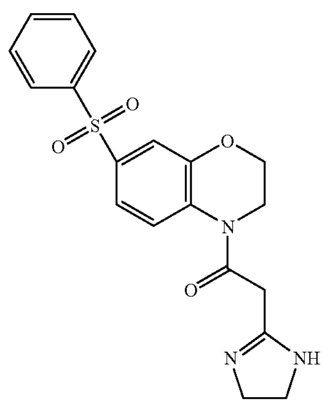 | 1-(7-Benzenesulfonyl-2,3-dihydro-benzo[1,4]oxazin-4-yl)-2-(4,5-dihydro-1H-imidazol-2-yl)-ethanone | 44.0–47.0° C. | 6 |
| 21 | 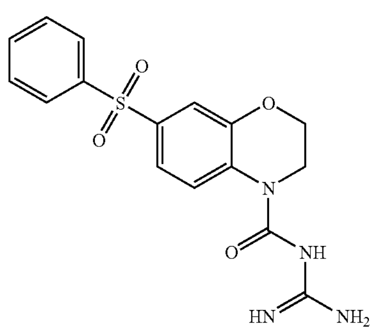 | N-(7-Benzenesulfonyl-2,3-dihydro-benzo[1,4]oxazine-4-carbonyl)-guanidine | 61.2–67.3° C. | 7 |
| 22 | 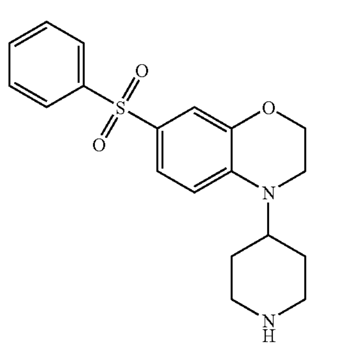 | 7-Benzenesulfonyl-4-piperidin-4-yl-3,4-dihydro-2H-benzo[1,4]oxazine | 251.9–253.2° C. | 11 |

TABLE 1-continued

| # | Structure | Name | MP° C./ M + H | Example |
|---|-----------|------|---------------|---------|
| 23 | 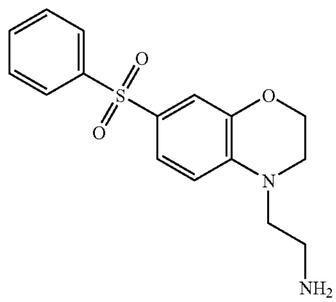 | 2-(7-Benzenesulfonyl-2,3-dihydro-benzo[1,4]oxazin-4-yl)-ethylamine | 261.0–265.1° C. | 4 |
| 24 | 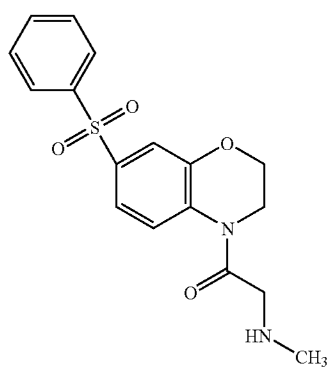 | 1-(7-Benzenesulfonyl-2,3-dihydro-benzo[1,4]oxazin-4-yl)-2-methylamino-ethanone | 219.9–220.9° C. | 10 |
| 25 | 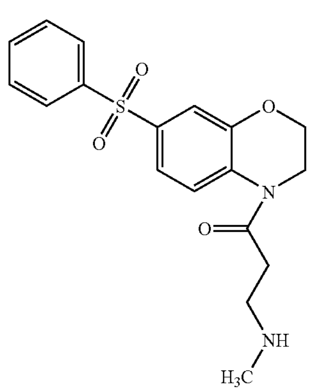 | 1-(7-Benzenesulfonyl-2,3-dihydro-benzo[1,4]oxazin-4-yl)-3-methylamino-propan-1-one | 361 (M + H) | 9 |
| 26 | 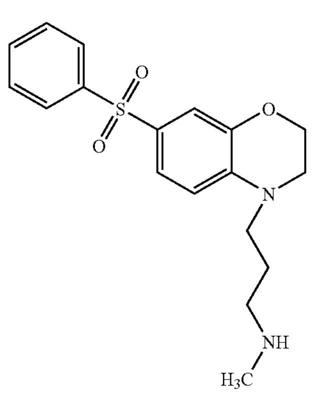 | [3-(7-Benzenesulfonyl-2,3-dihydro-benzo[1,4]oxazin-4-yl)-propyl]-methyl-amine | 188.3–193.2° C. | 9 |

TABLE 1-continued

| # | Structure | Name | MP° C./ M + H | Example |
|---|---|---|---|---|
| 27 | 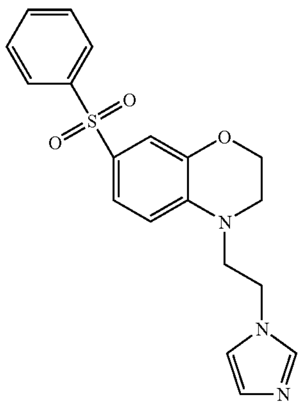 | 7-Benzenesulfonyl-4-(2-imidazol-1-yl-ethyl)-3,4-dihydro-2H-benzo[1,4]oxazine | 61.5–64.4° C. | 10 |
| 28 | 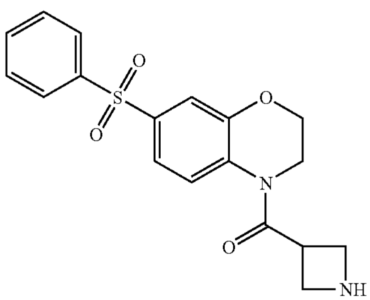 | Azetidin-3-yl-(7-benzenesulfonyl-2,3-dihydro-benzo[1,4]oxazin-4-yl)-methanone | 182.0–186.6° C. | 9 |
| 29 | 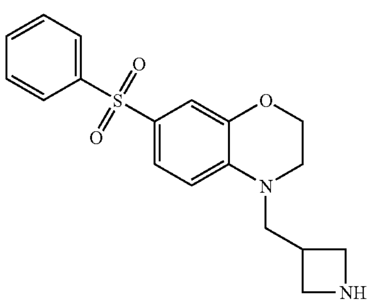 | 4-Azetidin-3-ylmethyl-7-benzenesulfonyl-3,4-dihydro-2H-benzo[1,4]oxazine | 194.9–196.0° C. | 9 |
| 30 | 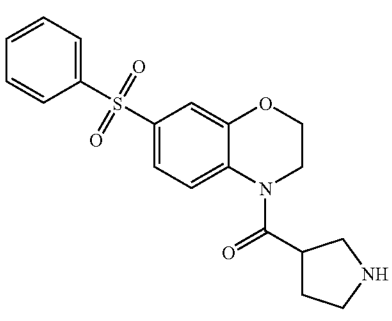 | (7-Benzenesulfonyl-2,3-dihydro-benzo[1,4]oxazin-4-yl)-pyrrolidin-3-yl-methanone | 373 (M + H) | 9 |

TABLE 1-continued

| # | Structure | Name | MP° C./ M + H | Example |
|---|---|---|---|---|
| 31 | 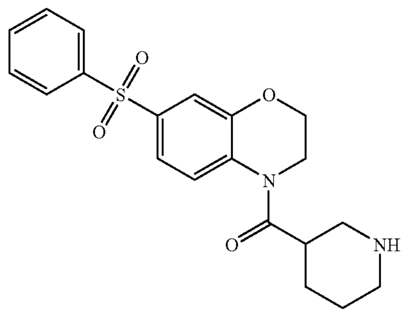 | (7-Benzenesulfonyl-2,3-dihydro-benzo[1,4]oxazin-4-yl)-piperidin-3-yl-methanone | 387 (M + H) | 9 |
| 32 | 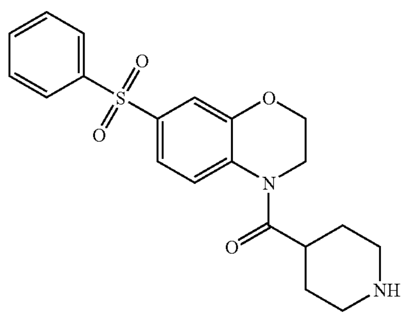 | (7-Benzenesulfonyl-2,3-dihydro-benzo[1,4]oxazin-4-yl)-piperidin-4-yl-methanone | 387 (M + H) | 9 |
| 33 | 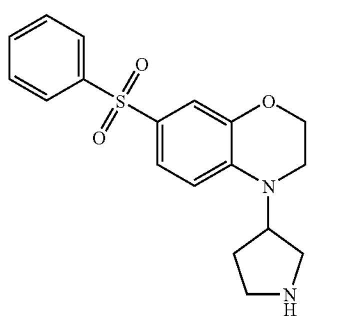 | 7-Benzenesulfonyl-4-pyrrolidin-3-yl-3,4-dihydro-2H-benzo[1,4]oxazine | 345 (M + H) | 12 |
| 34 | 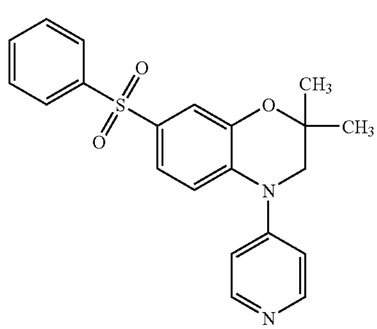 | 7-Benzenesulfonyl-2,2-dimethyl-4-pyridin-4-yl-3,4-dihydro-2H-benzo[1,4]oxazine | 381 (M + H) | 13 |

TABLE 1-continued

| # | Structure | Name | MP° C./ M + H | Example |
|---|---|---|---|---|
| 35 | 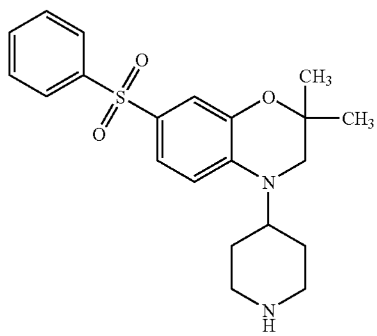 | 7-Benzenesulfonyl-2,2-dimethyl-4-piperidin-4-yl-3,4-dihydro-2H-benzo[1,4]oxazine | 388 (M + H) | 13 |
| 36 | 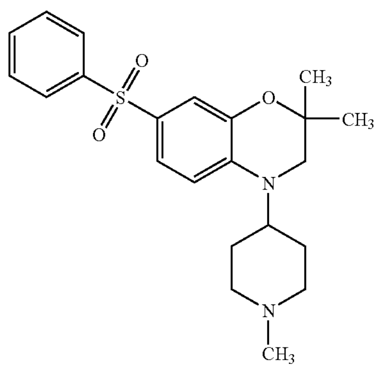 | 7-Benzenesulfonyl-2,2-dimethyl-4-(1-methyl-piperidin-4-yl)-3,4-dihydro-2H-benzo[1,4]oxazine | 402 (M + H) | 13 |
| 37 | 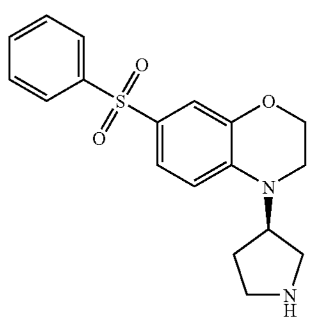 | (R)-7-Benzenesulfonyl-4-pyrrolidin-3-yl-3,4-dihydro-2H-benzo[1,4]oxazine | 138.5–140.0° C. | 13 |
| 38 | 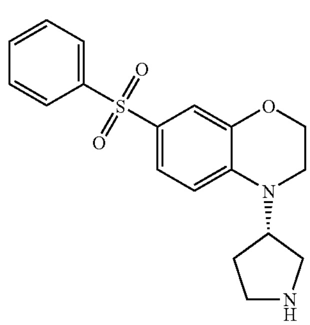 | (S)-7-Benzenesulfonyl-4-pyrrolidin-3-yl-3,4-dihydro-2H-benzo[1,4]oxazine | 145.3–146.9° C. | 13 |

Another aspect of the invention provides a composition comprising a therapeutically effective amount of at least one compound of formula (I) and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein L is a leaving group that may be the same or different in each occurrence, and k, m, n, p, $R^1$, $R^2$, $R^3$, $R^5$, $R^6$, $R^7$, and $R^8$ are as defined herein. Numerous synthetic routes to benzoxazines are known and may be used in preparation of the subject compounds, and the procedure of Scheme A is only exemplary. Specific examples of the procedure of Scheme A are provided in the following Experimental section.

SCHEME A

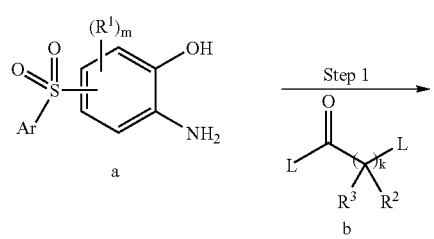

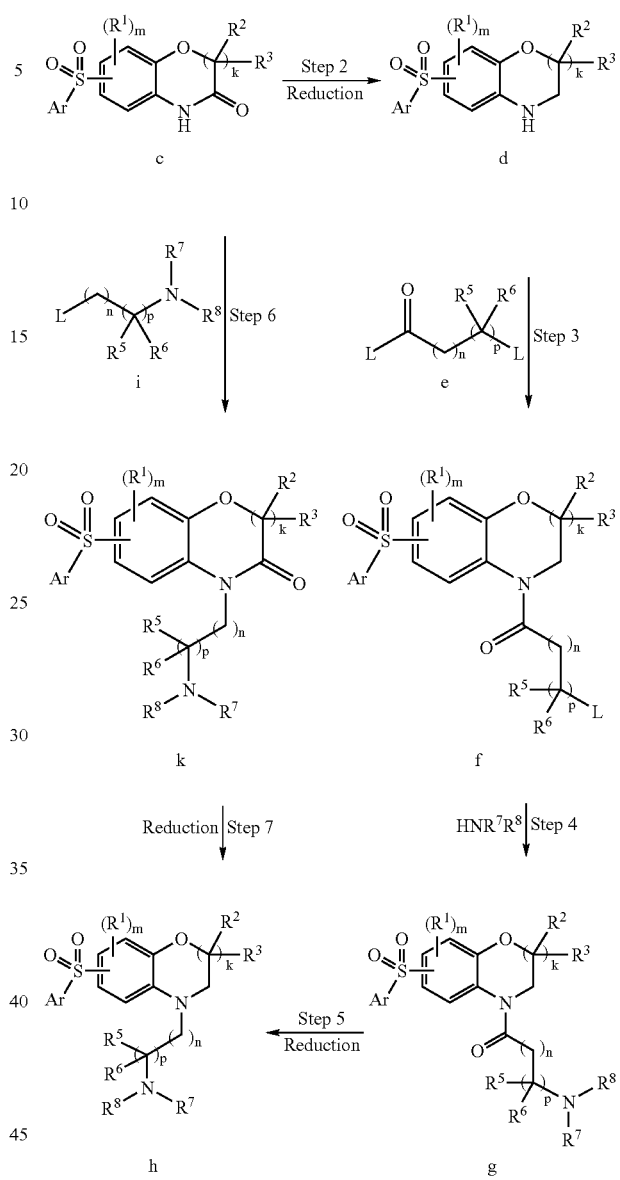

In step 1 of Scheme A, arylsulfonyl aminophenol a is treated with acyl compound b to afford arylsulfonyl benzoxazinone c. Arylsulfonyl aminophenol a can be prepared by a variety of known procedures. Exemplary syntheses of arylsulfonyl aminophenols are described by Makosza et al. in *Journal of Organic Chemistry*, 63(3) 1998, 4199-4208. Each L may independently be any leaving group, such as halo, tolsyl and the like. Selection of the appropriate acyl compound b allows preparation of six-membered (k=1) and seven-membered (k=2) benzoxazines with a variety of possible $R^2$ and $R^3$ substituents. For example, 2-chloroacetyl chloride provides a six-membered benzoxazine with $R^2$ and $R^3$ being hydrogen, 3-chloropropionyl chloride provides a seven-membered benzoxazine with $R^2$ and $R^3$ being hydrogen, 2-bromo-2-methyl-propionyl chloride provides a six-membered benzoxazine with $R^2$ and $R^3$ both as methyl, and 2-bromobutanoyl chloride provides a six-membered benzoxazine wherein one of $R^2$ and $R^3$ is hydrogen and the other is ethyl.

In step 2, arylsulfonyl benzoxazinone c undergoes reduction to yield arylsulfonyl benzoxazine d. This reduction may be carried out, for example, using borane or a borane complex under dry polar aprotic solvent conditions, followed by treatment with acid.

An N-acylation is carried out in step 3 by treatment of arylsulfonyl benzoxazine d with acyl compound e, to provide an N-acylated arylsulfonyl benzoxazine f, which is a compound of formula I in accordance with the invention. In acyl compound e, L may be any leaving group, such as halo or tolsy. Acyl compound e may comprise, for example, 2-chloroacetyl chloride, 3-chloropropionyl chloride provides a seven-membered benzoxazine with $R^2$ and $R^3$ being hydrogen, 2-bromo-2-methyl-propionyl chloride, 2-bromobutanoyl chloride, and the like. The acylation reaction of step 3 may be carried out under polar solvent conditions in the presence of mild base.

In step 4, N-acyl arylsulfonyl benzoxazine f, is treated with amine $HNR^7R^8$ to afford an aminoacyl benzoxazine compound g. Compound g is a compound of formula I in accordance with the invention. The amination reaction of step 4 may be carried out in methanol or other polar protic solvent.

In optional step 5, aminoacyl benzoxazine compound g. may undergo reduction to provide benzoxazine compound h, which is also a compound of formula I in accordance with the invention. This reduction may be carried out, for example, using borane or a borane complex under dry polar aprotic solvent conditions, followed by treatment with acid.

In an alternative procedure, steps 2 through 5 of Scheme A may be omitted, and steps 6 and 7 carried out instead. In step 6, arylsulfonyl benzoxazinone c is treated with alkyating agent j to provide an N-alkyl benzoxazinone j. This alkylation may be carried out, for example, under polar aprotic solvent conditions in the presence of mild base. In step 7, N-alkyl benzoxazinone j is reduced to benzoxazine h which, as related above, is a compound of formula I. This reduction may be achieved under the same conditions used for the reduction reaction of step 2. It should be noted that reduction of the carbonyl group of compound g in optional step 5 results in an increase of one to the integer value of n.

Many variations on the procedure of Scheme A are possible and will be readily apparent to those skilled in the art. For example, acyl compound e may include an amino, alkylamino, dialkylamino, or other functionality thereon, such that step 4 may be omitted. In another variation, a nitrile group may be present on alkylating agent j in place of the —$NR^7R^8$ functionality, with the nitrile group subsequently reduced or subject to cyclization reaction to provide an amine functionality. Where $R^7$ and/or $R^8$ is hydrogen, suitable protection and deprotection strategies may be employed.

Referring to Scheme B, another synthetic route for the subject compounds is shown, wherein PG is a protecting group and may be the same or different on each occurrence, L is a leaving group that may be the same or different in each occurrence, and k, m, u, v, $R^1$, $R^2$ and $R^3$ are as defined herein.

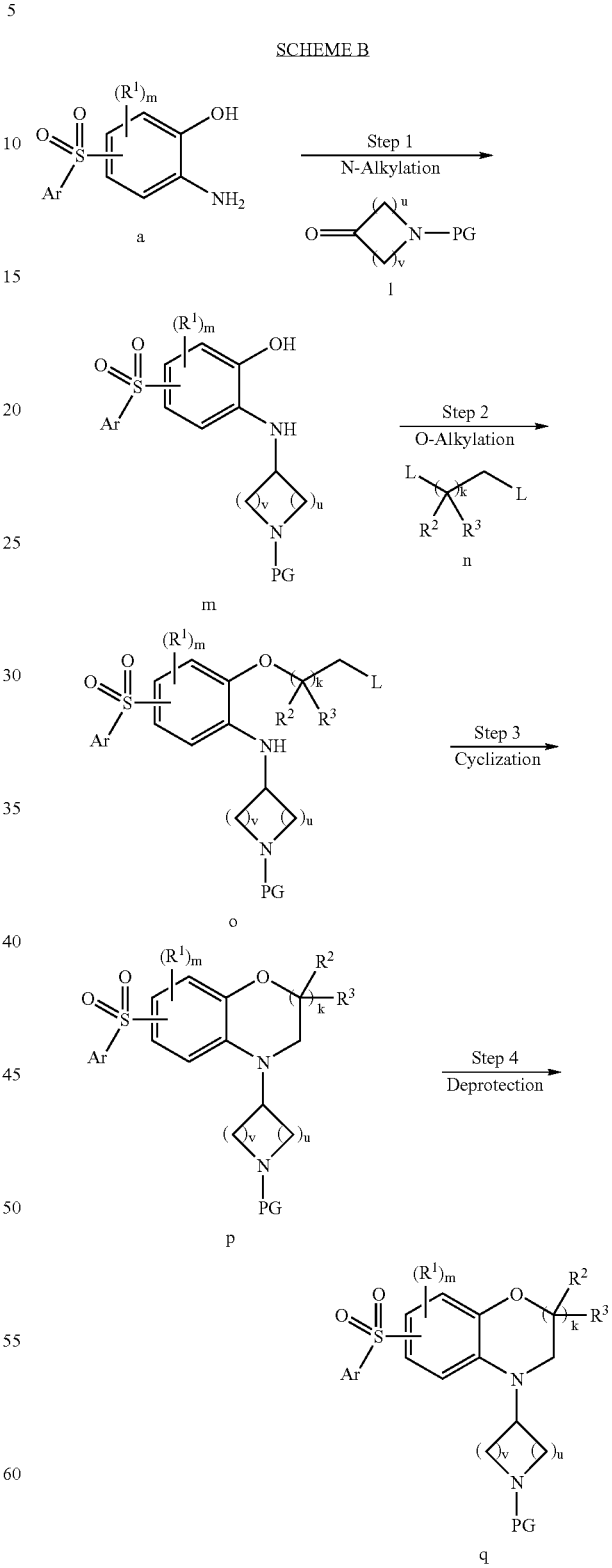

In step 1 of Scheme B, arylsulfonyl aminophenol a is reacted with an N-protected cyclic ketone 1 to yield an arylsulfonyl cycloamino aminophenol m. This N-alkylation reaction may be achieved in polar aprotic solvent under mildly reducing conditions. Cyclic ketone may comprise, for example, Boc-azetidinone, Boc-pyrrolidinone, Boc-piperidinone, and the like.

In step 2 an O-alkylation is carried out by reaction of aminophenol m with alkylating agent n to furnish compound o. Alkylating agent n may comprise, for example, 1-bromo-2-chloroethane (to provide k=1 and $R^2$, $R^3$ as hydrogen), 1-bromo-3-chloropropane (to provide k=2 and $R^2$, $R^3$ as hydrogen), 2-bromo-2-methyl-1-chloro propane (to provide k=1 and $R^2$, $R^3$ as methyl), and the like. The O-alkylation of step 2 may be achieved under polar aprotic solvent conditions in the presence of mild base.

A cyclization occurs in step 3 and is effected by treating compound o with sodium iodide under dry polar aprotic conditions, followed by strong base such as alkalai metal hydride, to afford arylsulfonyl benzoxazinone p. Arylsulfonyl benzoxazinone p is then deprotected in step 4 to provide benzoxazine a, which is a compound of formula I in accordance with the invention.

As in the case of Scheme A, many variations on the procedure of Scheme B are possible and will suggest themselves to those skilled in the art. More specific details for producing compounds of formula I are described in the Examples section below.

Utility

The compounds of the invention have selective affinity for 5-HT receptors, including the $5\text{-}HT_6$ the $5\text{-}HT_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding and functional assays are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pennsylvania. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof.

Preparation 1

7-Benzenesulfonyl-3,4-dihydro-2H-benzo[1,4]oxazine

The synthetic procedures described in this Preparation were carried out according to the process shown in Scheme C

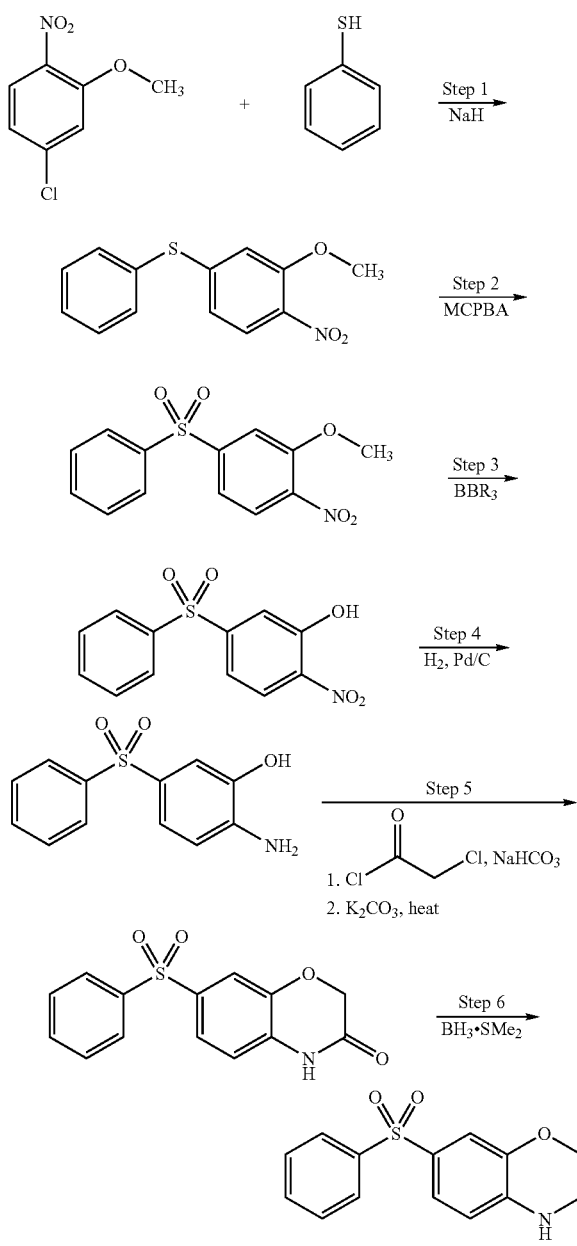

Step 1:

2-Methoxy-1-nitro-4-phenylsulfanyl-benzene

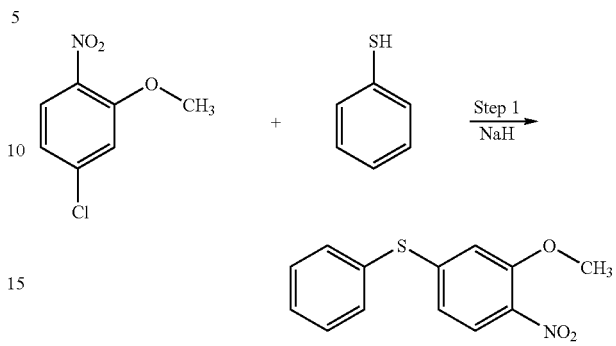

Using the procedure reported in *Chem. Pharm. Bull.* 40(2), 351-6, 1992, sodium hydride (60% suspension in mineral oil, 1.26 g, 44 mmol) was added to 40 mL of dimethyl formamide (DMF) at 0° C., and a solution of benzenethiol (2.25 g, 22 mmol) in 5 mL of DMF was added dropwise over five minutes, followed by stirring for 30 minutes. A solution of 4-chloro-2-methoxy-1-nitro-benzene (3.25 g, 20 mmol) in 25 mL of DMF was then added dropwise to the reaction mixture over 30 minutes, after which stirring was continued for another hour. Sixty mL of water was added to the reaction mixture, and a solid precipitated and was collected and dried under vacuum to yield 4.63 g (17.7 mmol, 89%) of 2-methoxy-1-nitro-4-phenyl-sulfanyl-benzene. MS: 262 (M+H)$^+$.

Step 2:

4-Benzenesulfonyl-2-methoxy-1-nitro-benzene

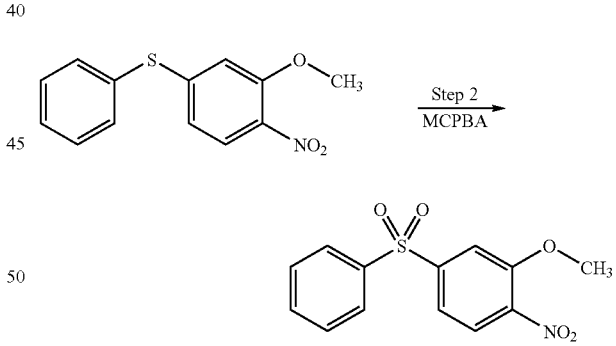

2-Methoxy-1-nitro-4-phenylsulfanyl-benzene (4.63 g, 18.7 mmol) was dissolved in methylene chloride, and the solution was cooled to 0° C. Meta-chloroperbenzoic acid (8.73 gm 39 mmol) was added to this reaction mixture in four portions over a 10 minute period, after which the reaction mixture was stirred for 2 hours. A solid formed during stirring, and was removed by filtration. The filtrate was diluted with 20 mL of methylene chloride, and was washed three times with 45 mL of saturated NaHCO$_3$, dried (MgSO$_4$), and concentrated in vacuo to yield 4.69 g of 4-benzenesulfonyl-2-methoxy-1-nitro-benzene as a yellow solid (16 mmol, 90.3%). MS: 294 (M+H)$^+$.

Step 3:

5-Benzenesulfonyl-2-nitro-phenol

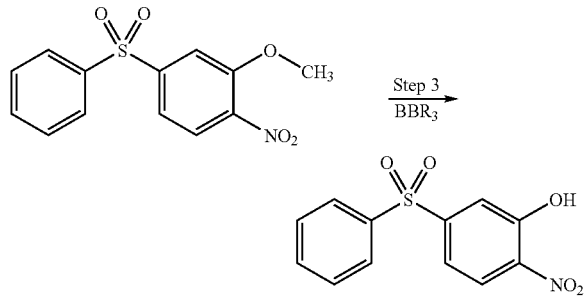

A solution of 4-benzenesulfonyl-2-methoxy-1-nitro-benzene (4.69 g, 16 mmol) was dissolved in 250 mL of methylene chloride and cooled to 0° C. BBr$_3$ (64 mL, 1M in methylene chloride) was added dropwise to the reaction mixture over 30 minutes. Stirring was continued, and the reaction mixture was allowed to warm up to room temperature. Methylene chloride (200 mL) was added to the reaction mixture and the organic layer was washed twice with 450 mL of water, once with 200 mL of saturated NaHCO$_3$, dried (MgSO$_4$) and concentrated in vacuo. The residue was recrystallized from ethanol to afford 3.206 g (11.5 mmol, 72%) of 5-benzenesulfonyl-2-nitro-phenol as a yellow solid. MS: 280 (M+H)$^+$.

Step 4:

2-Amino-5-benzenesulfonyl-phenol

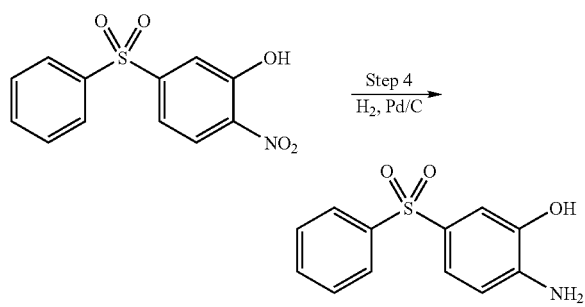

To a 1 liter flask was added 500 mg of a 5% dispersion of palladium metal on charcoal. The solid was wetted with 40 mL of ethanol and the flask was charged with a solution of 5-benzenesulfonyl-2-nitro-phenol (17.35 g., 62.1 mmol) in 350 mL ethanol. The flask was purged with hydrogen gas and a pressure of 1 Atm was maintained for 2 hours. The reaction mixture was filtered through celite, the filtrate concentrated in vacu, and the resulting residue was purified by flash (1:1:2 of "magic base" (6:1:0.1 methylene chloride: methanol:ammonia):CH$_2$Cl$_2$:hexanes.) The resulting solid was recrystallized from 300 mL EtOAc to give 7.68 g (31 mmol, 50%) of 2-amino-5-benzenesulfonyl-phenol as crystalline solid. MS: 250 (M+H)$^+$.

Step 5:

7-Benzenesulfonyl-4H-benzo[1,4]oxazin-3-one

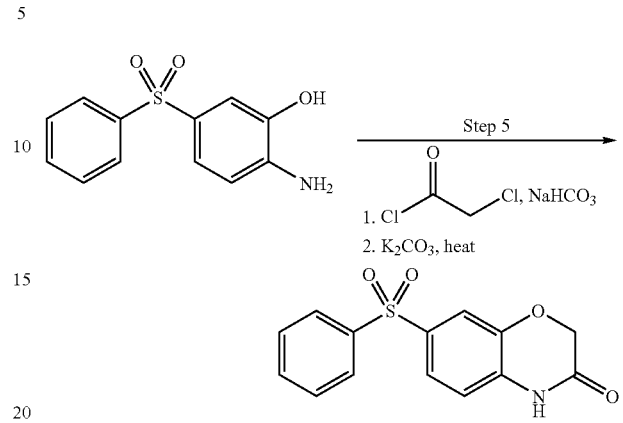

A solution of 2-amino-5-benzenesulfonyl-phenol (0.392 g., 1.57 mmol) in 10 mL of acetonitrile was cooled to O° C. To this solution was added sodium bicarbonate (0.263 g., 3.14 mmol) in 4 mL water. With stirring, 2-chloroacetyl chloride (0.162 mL, 2.097 mmol) was added dropwise over 2 minutes. Stirring was continued for one hour as the reaction mix was warmed to room temperature. Potassium carbonate (0.261 g., 1.89 mmol) was then added and the system was warmed to reflux (85° C.) for two hours. The reaction mixture was added to 50 mL EtOAc, the aqueous fraction was separated and the organic layer was washed twice with 50 mL water, dried over Na$_2$SO$_4$ and concentrated in vacuo. The crude solid was recrystallized from a mixture of 30 mL each of ethanol and water to give 0.382 g (1.32 mmol, 84%) of 7-benzenesulfonyl-4H-benzo[1,4]oxazin-3-one as a yellow solid. MS: 288 (M–H)$^-$.

Step 6:

7-Benzenesulfonyl-3,4-dihydro-2H-benzo[1,4]oxazine

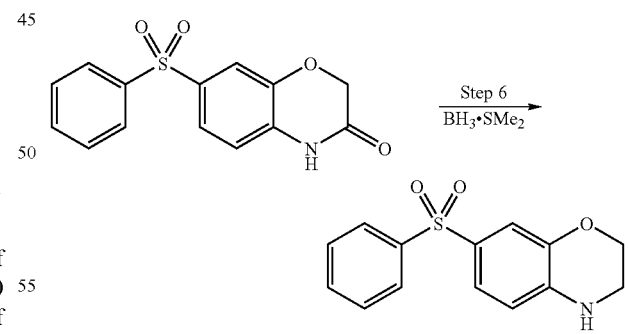

A suspension of 7-benzenesulfonyl-4H-benzo[1,4]oxazin-3-one (2.314 g., 8.00 mmol) in 30 ml anhydrous THF was brought to reflux, and borane-dimethyl sulfide complex (2.4 mL, 10 M solution) was added dropwise via syringe. The solution was refluxed for two hours, at which time the solution was cooled to room temperature and ethanolic HCl (10 mL., 2 N solution) was added dropwise. The resulting solution was refluxed for 3 hours and allowed to cool to room temperature. The reaction mixture was poured into 100 mL water, the resulting solution made basic with potassium carbonate and extracted three times with 50 mL Et₂O. The organic fractions were washed with 100 mL brine, dried over Na₂SO₄ and concentrated in vacuo. The resulting residue was purified by flash chromatography (20 to 50% EtOAc in hexanes) to give 1.75 g of 7-benzenesulfonyl-3,4-dihydro-2H-benzo[1,4]oxazine (79.5%) as a yellow solid. MS: 276 (M+H)⁺.

Preparation 2

6-Benzenesulfonyl-3,4-dihydro-2H-benzo[1,4]oxazine

The synthetic procedures described in this Example were carried out according to the process shown in Scheme D.

SCHEME D

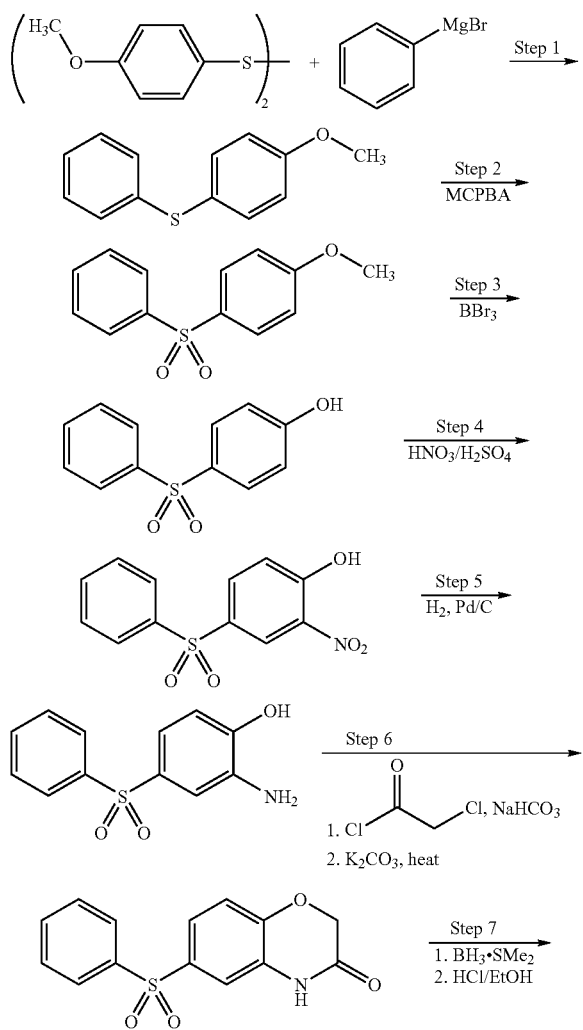

Step 1:

1-Methoxy-4-phenylsulfanyl-benzene

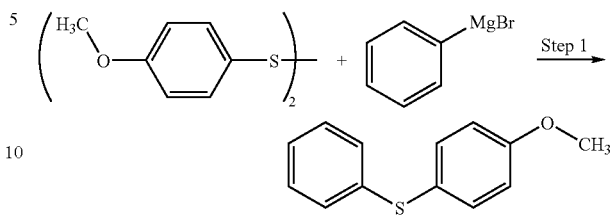

4-Methoxyphenyl disulfide (9.014 g, 32.37 mmol) was dissolved in 15 mL of dry tetrahydrofuran (THF) under nitrogen, and the reaction mixture was cooled to 0° C. Phenylmagnesium bromide (16.18 mL, 3.0M in THF) was added dropwise to the reaction mixture via syringe over 15 minutes, after which the reaction mixture was warmed to room temperature. The reaction mixture was washed with 50 mL Et₂O, and the combined organic layer was washed three times with 50 mL water, once with 50 mL saturated NH₄Cl, and twice with 50 mL of 2N NaOH. The organic layer was dried (Na₂SO₄), concentrated in vacuo, and the residue was purified by flash chromatography (0 to 3% ethyl acetate in hexanes) to yield 5.506 g (25.45 mmol, 79%) of 1-methoxy-4-phenylsulfanyl-benzene as a clear oil. MS: 217 (M+H)⁺.

Step 2:

1-Benzenesulfonyl-4-methoxy-benzene

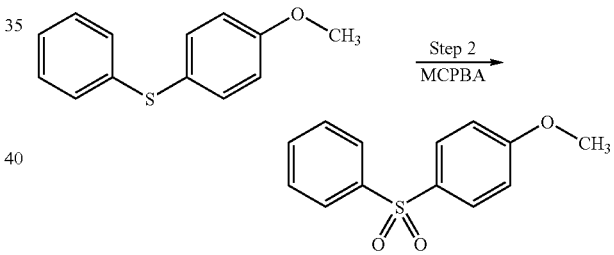

1-Methoxy-4-phenylsulfanyl-benzene (5.506 g, 25.45 mmol), was dissolved in 15 mL methylene chloride and cooled to 0° C. Meta-chloroperbenzoic acid (12.6 g, 56 mmol) was added in portions over 15 minutes to the stirring reaction mixture. The mixture was stirred for an additional 2 hours at room temperature, and then filtered. The solid was discarded and the filtrate was washed twice with 45 mL of 2M K₂CO₃ solution, dried (Na₂SO₄) and concentrated in vacuo to provide 1-benzenesulfonyl-4-methoxy-benzene (5.592 g, 94%) as a white solid. MS: 249 (M+H)⁺.

Step 3:

4-Benzenesulfonyl-phenol

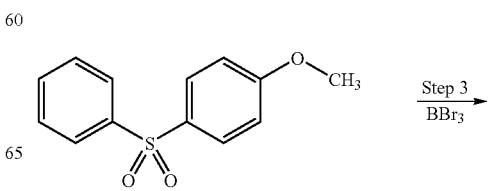

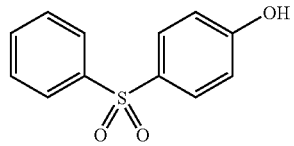

1-Benzenesulfonyl-4-methoxy-benzene (5.92 g, 23.8 mmol) was dissolved in methylene chloride and stirred. A solution of BBr$_3$ (6.77 g, 71.68 mg) in 120 mL of methylene chloride was added dropwise to the reaction mixture, after which the mixture was stirred for 4 hours at room temperature. Water (150 mL) was then added to the reaction mixture, and the organic layer was separated. The aqueous layer was extracted three times with 45 mL methylene chloride, and the combined organic layers were dried (Na$_2$SO$_4$) and concentrated in vacuo. The residue was purified by flash chromatography (30-50% EtOAc in hexanes) to afford 5.348 g of 4-benzenesulfonyl-phenol (22.8 mmol, 99%) as an oil. MS: 235 (M+H)$^+$.

Step 4:

4-Benzenesulfonyl-2-nitro-phenol

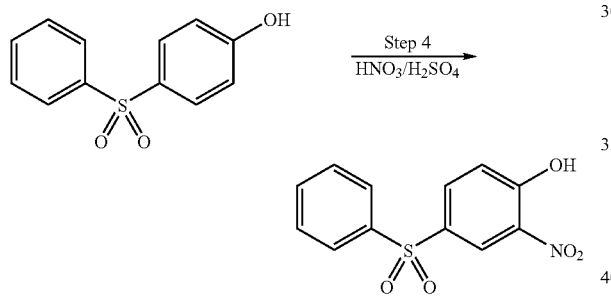

Using the procedure of *J. Org. Chem.* 59(15) 1994, 4301, 4-benzenesulfonyl-phenol (5.348 g, 22.8 mmol) was added to 3.07 mL of conc. H$_2$SO$_4$ with stirring. Concentrated HNO$_3$ (1.28 g) was added dropwise via addition funnel, and the reaction mixture was stirred under nitrogen for 4 hours. The reaction mixture was then poured over ice, and the resulting suspension was extracted four times with 50 mL of methylene chloride. The combined organic layers were dried (Na$_2$SO$_4$) and concentrated in vacuo to yield an oil which slowly solidified. The solid was washed with 1:1 EtOAc:hexanes to yield 4-benzenesulfonyl-2-nitro-phenol (6.37 g, quantitative) as a crude solid. MS: 235 (M+H)$^+$.

Step 5:

2-Amino-4-benzenesulfonyl-phenol

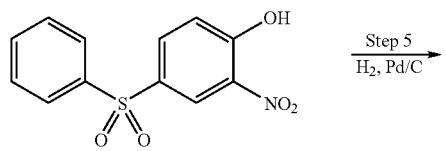

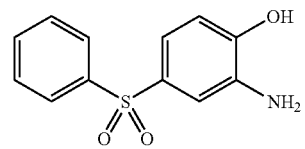

4-Benzenesulfonyl-2-nitro-phenol (6.37 g, 22.8 mmol), Pd/C (5%, 3 mg) and 1 mL of water were added to a flask, after which 45 mL of EtOH was added. The reaction mixture was stirred and purged with H$_2$ (1 Atm). The reaction mixture was stirred under H$_2$ for 4 hours, then filtered through celite. The filtrate was concentrated in vacuo to yield a crude oil, which was purified by flash chromatography (0-15% "magic base" (6:1:0.1 methylene chloride:methanol:ammonia) in dichloromethane) to afford 2-amino-4-benzenesulfonyl-phenol (2.695 g, 39%). MS: 250 (M+H)$^+$.

Step 6:

6-Benzenesulfonyl-4H-benzo[1,4]oxazin-3-one

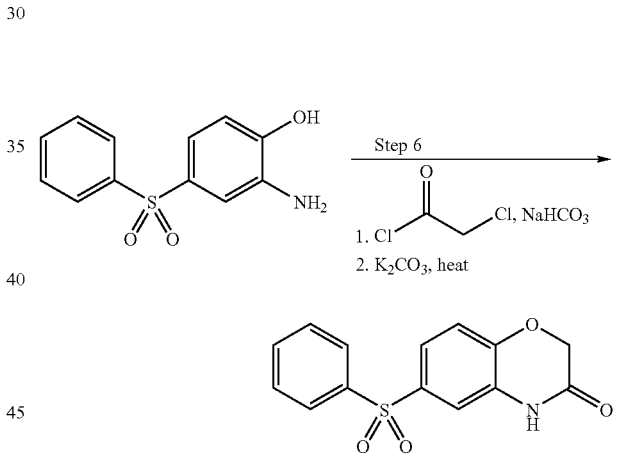

2-Amino-4-benzenesulfonyl-phenol (2.064 g, 8.2 mmol) was dissolved in 15 mL of methyl ethyl ketone, and NaHCO$_3$ (1.39 g, 9.1 mmol) was added to this solution. The reaction mixture was cooled to 0° C., and 2-chloroacetyl chloride (0.215 mL, 9.0 mmol) was added dropwise while stirring. The reaction mixture was stirred for 2 hours, after which K$_2$CO$_3$ (1.37 g, 9.95 mmol) was added, and the reaction was brought to reflux for three hours. The reaction mixture was cooled and 150 mL of EtOAc was added. The organic layer was washed three times with 50 ml water, once with 50 mL saturated brine, dried (Na$_2$SO$_4$) and concentrated in vacuo to yield a crude solid, which was purified by flash chromatography (10-30% EtOAc in hexanes), to afford 6-benzenesulfonyl-4H-benzo[1,4]oxazin-3-one (2.176 g, 7.52 mmol, 92%). MS: 290 (M+H)$^+$.

Step 7:

6-Benzenesulfonyl-3,4-dihydro-2H-benzo[1,4]oxazine

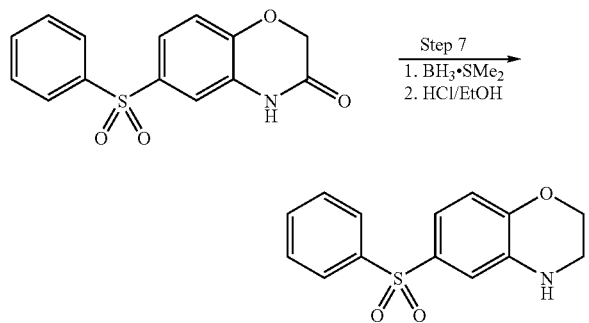

A suspension of 6-benzenesulfonyl-4H-benzo[1,4]oxazin-3-one (1.42 g g., 4.9 mmol) in 10 ml anhydrous THF was brought to reflux, and borane-dimethyl sulfide complex (2.45 mL, 10 M in THF, 24.5 mmol) was added dropwise via syringe. The solution was refluxed for 3 hours, and the solution was cooled to room temperature and ethanolic HCl (3 mL, 2 N) was added dropwise. The resulting solution was refluxed for 1 hour and then cooled to room temperature. The reaction mixture was poured into 50 mL water, the resulting solution made basic with potassium carbonate and extracted three times with 25 mL Et$_2$O. The organic fractions were washed with 50 mL brine, dried over Na$_2$SO$_4$ and concentrated in vacuo. The resulting residue was purified by flash chromatography (30 to 50% EtOAc in hexanes) to give 1.12 g of 6-benzenesulfonyl-3,4-dihydro-2H-benzo[1,4]oxazine (83%) as a yellow solid. MS: 276 (M+H)$^+$.

Example 1

[2-(7-Benzenesulfonyl-2,3-dihydro-benzo[1,4]oxazin-4-yl)-ethyl]-dimethyl-amine

The synthetic procedure described in this Example was carried out according to the process shown in Scheme E.

SCHEME E

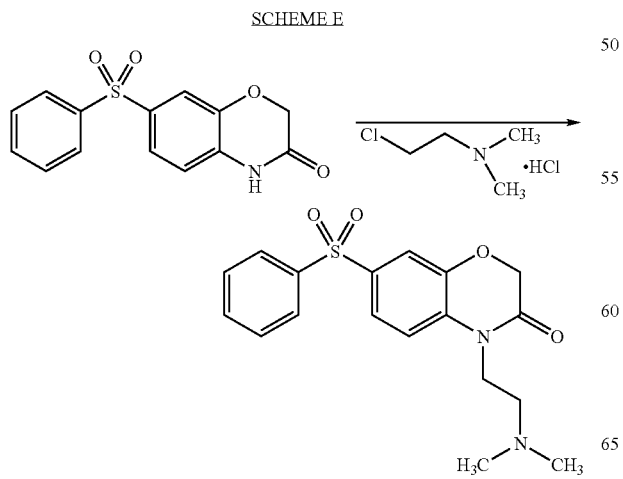

A suspension of 7-benzenesulfonyl-4H-benzo[1,4]oxazin-3-one (0.09 g., 0.3 mmol), (2-chloro-ethyl)-dimethyl-amine hydrochloride (0.056 g., 0.39 mmol) and potassium carbonate (0.095 g., 0.69 mmol) in 0.7 mL ethyl acetate was refluxed for 1 hour. To the reaction mixture was added 0.75 mL water, and reflux was continued for 3 hours. 30 mL Ethyl acetate was added, and the reaction mixture was washed three times with 15 mL water, dried over magnesium sulfate and concentrated in vacuo. The residue was purifed by flash chromatography (0 to 5% methanol in dichloromethane) to afford 0.055 g (0.15 mmol, 50%) of 7-benzenesulfonyl-4-(2-dimethylamino-ethyl)-4H-benzo[1,4]oxazin-3-one. MS: 361 (M+H)$^+$, mp: 232.9-235.3° C. (HCl salt).

The following compounds were similarly prepared using the appropriate aminoalkyl chloride in step 6 in place of (2-chloro-ethyl)-dimethyl-amine hydrochloride or replacing 7-benzenesulfonyl-4H-benzo[1,4]oxazin-3-one with 6-benzenesulfonyl-4H-benzo[1,4]oxazin-3-one:

7-Benzenesulfonyl-4-(3-dimethylamino-propyl)-4H-benzo[1,4]oxazin-3-one, MS: 375 (M+H)$^+$, mp: 194.0-196.4° C. (HCl salt);

7-Benzenesulfonyl-4-(4-dimethylamino-butyl)-4H-benzo[1,4]oxazin-3-one, MS: 389 (M+H)$^+$, mp: 179.0-180.0° C. (HCl salt); and 6-Benzenesulfonyl-4-(3-dimethylamino-ethyl)-4H-benzo[1,4]oxazin-3-one, MS: 361 (M+H)$^+$, mp: 204.0-206.9° C. (HCl salt).

Example 2

7-Benzenesulfonyl-4-(4,5-dihydro-1H-imidazol-2-ylmethyl)-4H-benzo[1,4]oxazin-3-one The synthetic procedures described in this Example were carried out according to the process shown in Scheme F.

SCHEME F

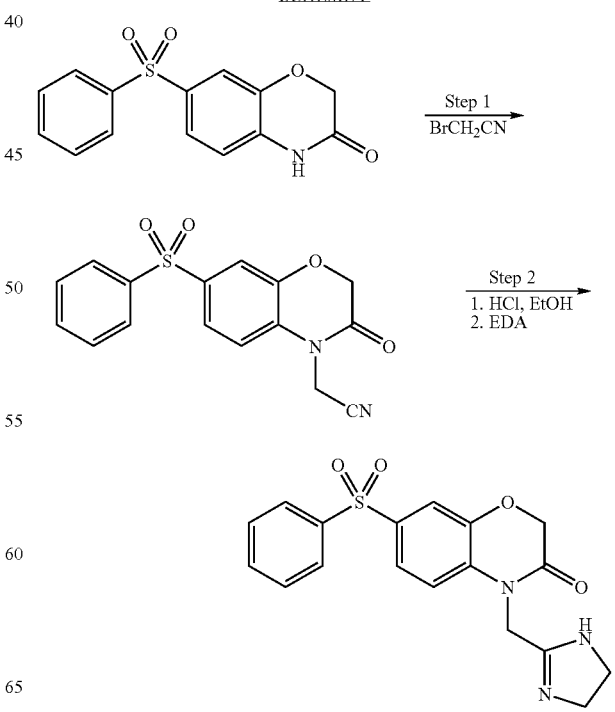

Step 1

(7-Benzenesulfonyl-3-oxo-2,3-dihydro-benzo[1,4]oxazin-4-yl)-acetonitrile

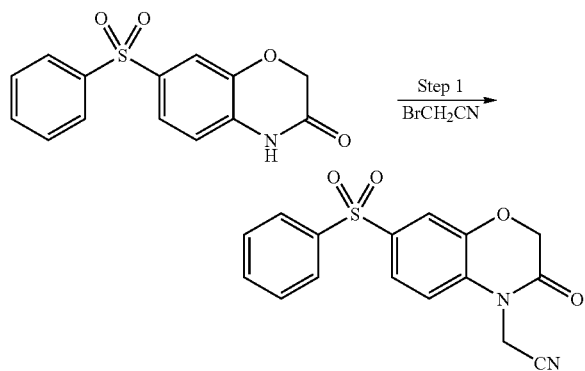

To a stirred suspension of sodium hydride (0.152 g. of a 60% dispersion in mineral oil, 3.8 mmol) in 5 mL DMF was added 7-benzenesulfonyl-4H-benzo[1,4]oxazin-3-one (1.0 g., 3.46 mmol). The resulting solution was allowed to stir for 20 minutes, and bromoacetonitrile (0.265 mL, 3.8 mmol) was added dropwise. The reaction mixture was stirred at room temperature for 2 hours, added to 45 mL water, and the resulting suspension was extracted twice with 30 mL ethyl acetate. The organic phase was washed with twice with 45 mL water, dried over magnesium sulfate, and concentrated in vacuo. The crude residue was purified by flash chromatography (20 to 30% ethyl acetate in hexanes) to give 1.06 g. (3.4 mmol, 89%) of (7-benzenesulfonyl-3-oxo-2,3-dihydro-benzo[1,4]oxazin-4-yl)-acetonitrile as a white solid. MS: 329 (M+H)$^+$.

Step 2

7-Benzenesulfonyl-4-(4,5-dihydro-1H-imidazol-2-ylmethyl)-4H-benzo[1,4]oxazin-3-one

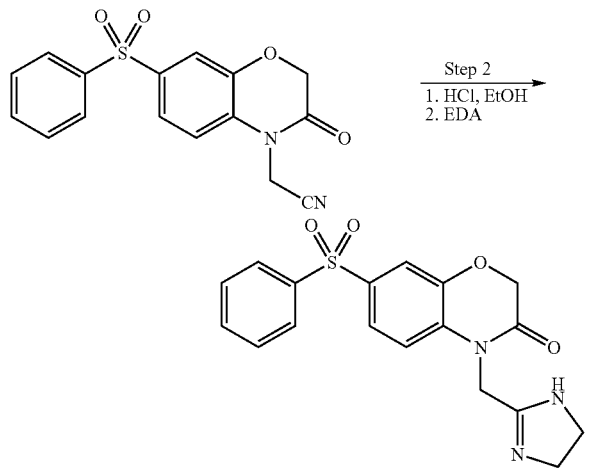

To a solution of (7-benzenesulfonyl-3-oxo-2,3-dihydro-benzo[1,4]oxazin-4-yl)-acetonitrile (0.156 g., 0.475 mmol) in 10 mL anhydrous chloroform was added ethanol (0.029 mL, 0.5 mmol), and the resulting solution was cooled in a water ice/acetone bath to −15° C. Hydrogen chloride gas was bubbled through the solution for 10 minutes, and the flask was sealed and kept at −15° C. for 18 hours. The reaction mixture was concentrated in vacuo and 0.5 Torr vacuum was applied to the residue for 2 hours. The crude imidate was dissolved in 5 mL anhydrous chloroform, and to this solution was added ethylene diamine (0.033 mL, 0.5 mmol) in 4 mL anhydrous chloroform and 5 mL ethanol. The resulting solution was stirred at room temperature for 3 hours, and was then concentrated in vacuo. The residue was purified by flash chromatography (30% "magic base" (6:1:0.1 methylene chloride:methanol:ammonia) in dichloromethane) to give 0.130 g (0.35 mmol, 74%) of 7-benzenesulfonyl-4-(4,5-dihydro-1H-imidazol-2-ylmethyl)-4H-benzo[1,4]oxazin-3-one as a clear oil. MS: 372 (M+H)$^+$, mp: 113.7-116.0° C. (HCl salt).

The following compounds were prepared in a similar fashion using the appropriate nitriles:

6-Benzenesulfonyl-4-(4,5-dihydro-1H-imidazol-2-ylmethyl)-4H-benzo[1,4]oxazin-3-one, MS: 372 (M+H)$^+$, mp: 250.0-252.0° C. (HCl salt);

1-(6-Benzenesulfonyl-2,3-dihydro-benzo[1,4]oxazin-4-yl)-2-(4,5-dihydro-1H-imidazol-2-yl)-ethanone, MS: 386 (M+H)$^+$ 44.0-47.0° C. (HCl salt);

1-(7-Benzenesulfonyl-2,3-dihydro-benzo[1,4]oxazin-4-yl)-2-(4,5-dihydro-1H-imidazol-2-yl)-ethanone, MS: 386 (M+H)$^+$, mp: 202.3-203.6° C. (HCl salt); and 6-Benzenesulfonyl-4-(4,5-dihydro-1H-imidazol-2-ylmethyl)-3,4-dihydro-2H-benzo[1,4]oxazine, MS: 358 (M+H)$^+$, mp: 114.0-116.1° C. (HCl salt).

Example 3

The synthetic procedure described in this Example was carried out according to the process shown in Scheme G.

SCHEME G

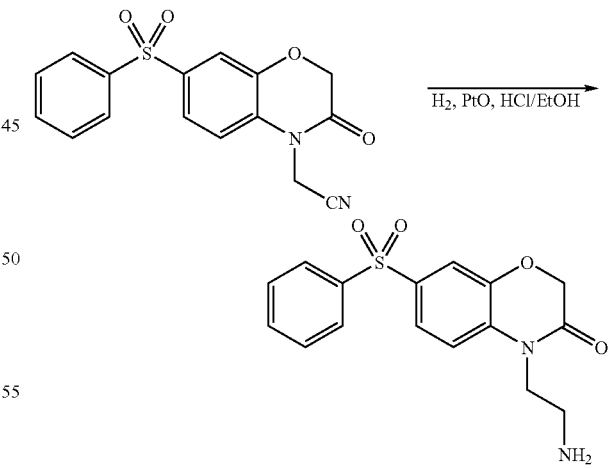

To a solution of 7-benzenesulfonyl-3-oxo-2,3-dihydro-benzo[1,4]oxazin-4-yl)-acetonitrile (1.0 g., 3.046 mmol) in 75 mL ethanol was added concentrated hydrogen chloride (1 mL, 12 mmol) and platinum oxide (0.020 g., 0.05 mmol). The suspension was treated with hydrogen gas at 50 psi for 48 hours, purged with nitrogen, heated to reflux to dissolve any solid present, and then filtered through celite. The celite was rinsed twice with 15 mL hot ethanol, and the combined filtrate was concentrated in vacuo to approximately 5 mL, at which point a precipitate was observed. The solution was cooled to 0° C. for 18 hours, and the solid was collected by filtration to afford 0.645 g (1.94 mmol, 64%) of 4-(2-amino-ethyl)-7-benzenesulfonyl-4H-benzo[1,4]oxazin-3-one hydrochloride as a fine off-white solid. MS: 333 (M+H)+, mp (hydrochloride): 206.9-209.1° C.

Example 4

The synthetic procedure described in this Example was carried out according to the process shown in Scheme H.

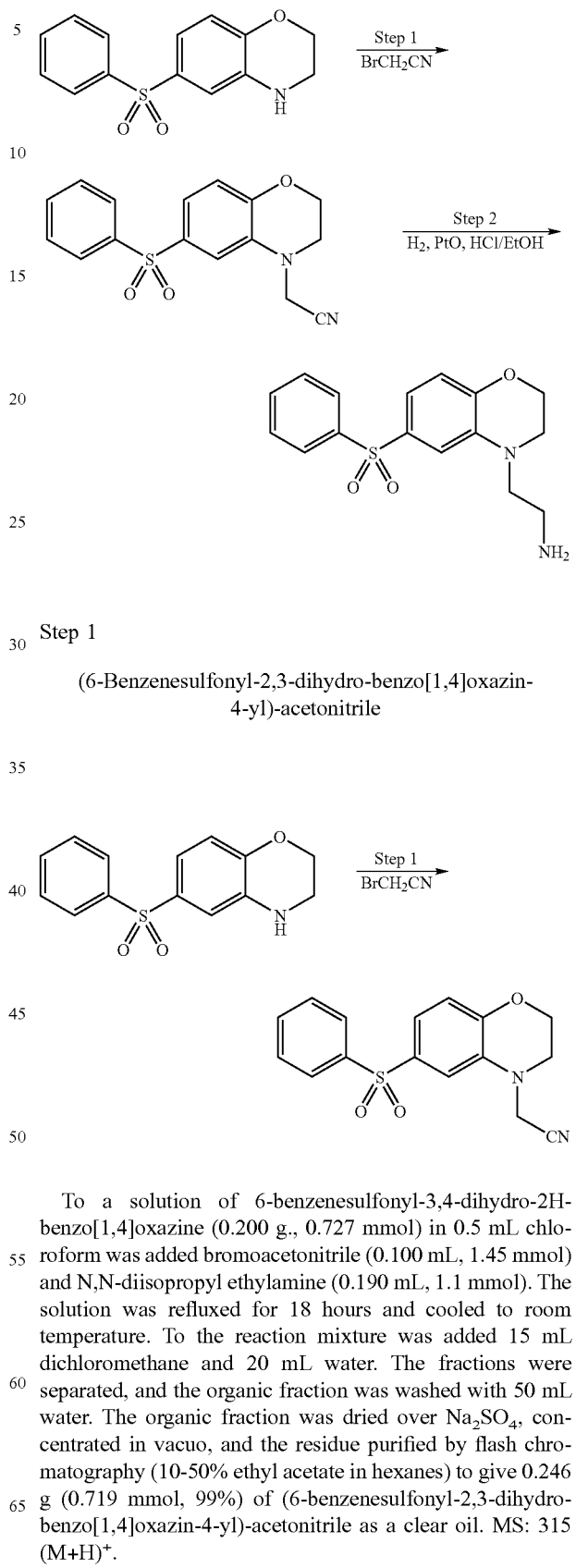

A solution of (7-benzenesulfonyl-3-oxo-2,3-dihydro-benzo[1,4]oxazin-4-yl)-acetonitrile (0.234 g., 0.713 mmol) in 2 mL anhydrous THF was warmed to reflux, and borane-methyl sulfide complex (0.5 mL of a 10 M solution, 5 mmol) was added dropwise over 5 minutes. Reflux was continued for 4 hours, and the reaction mixture was concentrated in vacuo. The residue was then dissolved in 2 mL ethanol and ethanolic hydrogen chloride was added (2 mL of a 2 N solution, 4 mmol.) The solution was refluxed for 18 hours then cooled to room temperature, resulting in formation of a precipitate. The solid was filtered and dried under vacuum for 18 hours to give 0.158 g (0.496 mmol, 70%) of 2-(7-benzenesulfonyl-2,3-dihydro-benzo[1,4]oxazin-4-yl)-ethylamine as a yellowish solid. MS: 319 (M+H)+, mp: 261.0-265.1° C. (HCl salt).

Similarly prepared was 2-(6-benzenesulfonyl-2,3-dihydro-benzo[1,4]oxazin-4-yl)-ethylamine, MS: 319 (M+H)+, mp (as hydrochloride): 242.9-245.9° C.

Example 5

6-Benzenesulfonyl-4-(4,5-dihydro-1H-imidazol-2-ylmethyl)-3,4-dihydro-2H-benzo[1,4]oxazine The synthetic procedures described in this Example were carried out according to the process shown in Scheme I.

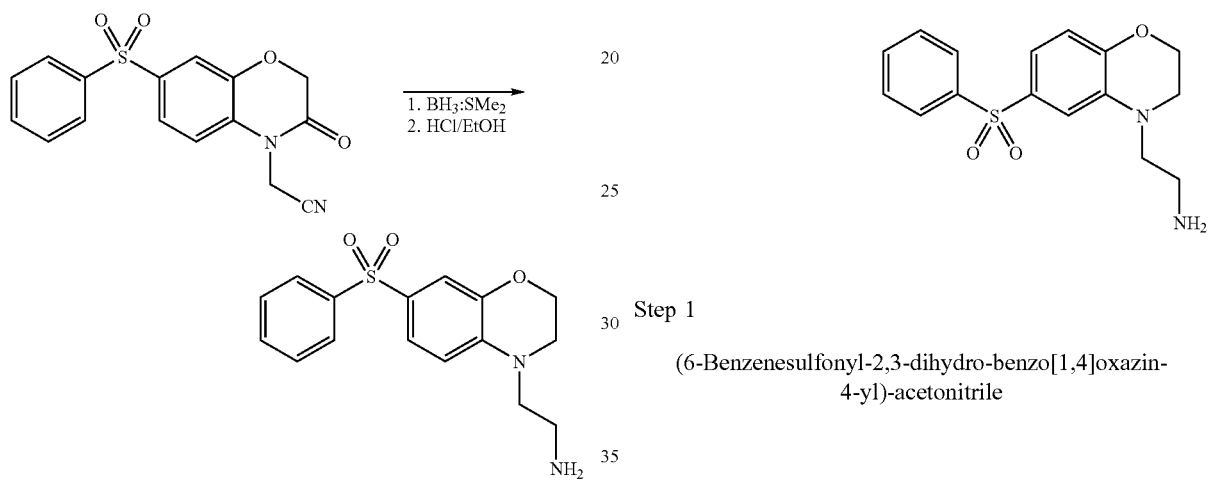

Step 1

(6-Benzenesulfonyl-2,3-dihydro-benzo[1,4]oxazin-4-yl)-acetonitrile

To a solution of 6-benzenesulfonyl-3,4-dihydro-2H-benzo[1,4]oxazine (0.200 g., 0.727 mmol) in 0.5 mL chloroform was added bromoacetonitrile (0.100 mL, 1.45 mmol) and N,N-diisopropyl ethylamine (0.190 mL, 1.1 mmol). The solution was refluxed for 18 hours and cooled to room temperature. To the reaction mixture was added 15 mL dichloromethane and 20 mL water. The fractions were separated, and the organic fraction was washed with 50 mL water. The organic fraction was dried over $Na_2SO_4$, concentrated in vacuo, and the residue purified by flash chromatography (10-50% ethyl acetate in hexanes) to give 0.246 g (0.719 mmol, 99%) of (6-benzenesulfonyl-2,3-dihydro-benzo[1,4]oxazin-4-yl)-acetonitrile as a clear oil. MS: 315 (M+H)+.

Step 2

2-(6-Benzenesulfonyl-2,3-dihydro-benzo[1,4]ox-azin-4-yl)-ethylamine

Step 1:

3-(6-Benzenesulfonyl-2,3-dihydro-benzo[1,4]ox-azin-4-yl)-3-oxo-propionitrile

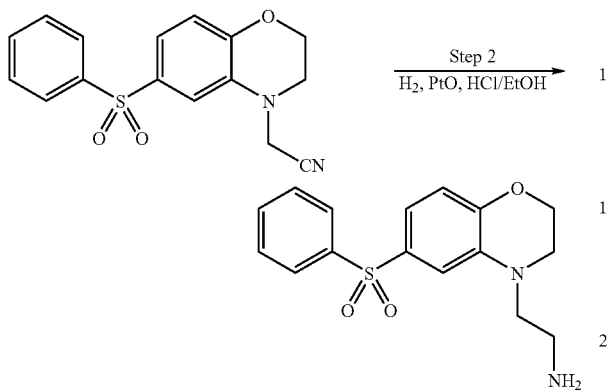

2-(6-Benzenesulfonyl-2,3-dihydro-benzo[1,4]oxazin-4-yl)-ethylamine was prepared using the procedure described above in Example 3. MS: 319 (M+H)$^+$, mp (HCl salt): 242.9-245.9° C.

Example 6

1-(6-Benzenesulfonyl-2,3-dihydro-benzo[1,4]ox-azin-4-yl)-2-(4,5-dihydro-1H-imidazol-2-yl)-etha-none The synthetic procedures described in this Example were carried out according to the process shown in Scheme J.

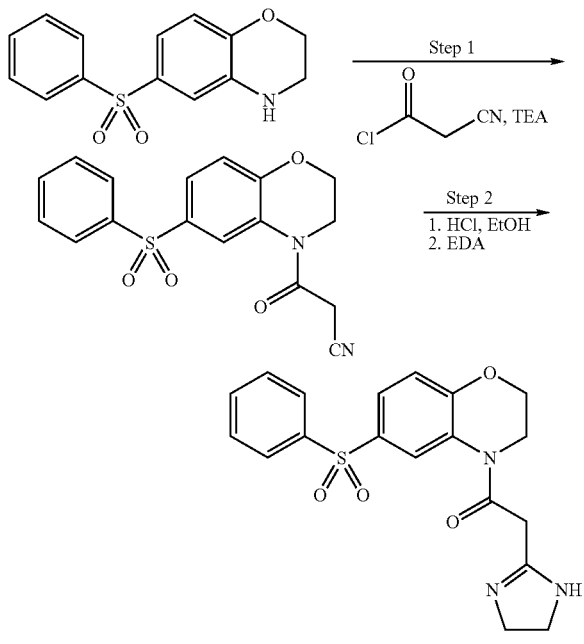

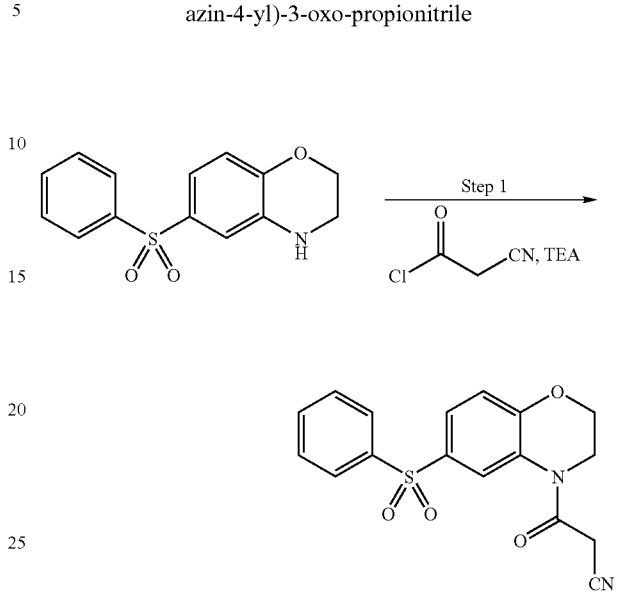

To a solution of α-cyanoacetic acid (0.085 g., 1.0 mmol) in 2 mL dichloromethane was added oxalyl chloride (0.262 mL, 3.0 mmol) and one drop N,N-dimethylformamide (~0.025 mL, cat). The solution is stirred for one hour, during which offgassing is observed, and concentrated in vacuo. The residue was dissolved in 4 mL dichloromethane and this solution was added dropwise to a solution of 6-benzene-sulfonyl-3,4-dihydro-2H-benzo[1,4]oxazine (0.275 g., 1.0 mmol) and triethylamine (0.152 mL, 1.1 mmol) in 3 mL dichloromethane at 0° C. The resulting solution was stirred for 2 hours, concentrated in vacuo and purified by flash chromatography to give 0.146 g (43%) of 3-(6-benzene-sulfonyl-2,3-dihydro-benzo[1,4]oxazin-4-yl)-3-oxo-propi-onitrile. MS: 343 (M+H)$^+$.

Similarly prepared was 3-(7-Benzenesulfonyl-2,3-dihy-dro-benzo[1,4]oxazin-4-yl)-3-oxo-propionitrile.

Also prepared by the above procedure, using the appropriate N-tertbutoxycarbonyl-protected carboxylic acids, and followed by deprotection of the product with ethanolic HCl, the following were prepared:

Azetidin-3-yl-(7-benzenesulfonyl-2,3-dihydro-benzo[1,4]oxazin-4-yl)-methanone, MS: 359 (M+H)$^+$, mp (as hydrochloride): 182.0-186.6° C. ° C.;

(7-Benzenesulfonyl-2,3-dihydro-benzo[1,4]oxazin-4-yl)-pyrrolidin-3-yl-methanone (racemic), MS: 373 (M+H)$^+$, mp: 109.2-110.5° C. (as hydrochloride);

(7-Benzenesulfonyl-2,3-dihydro-benzo[1,4]oxazin-4-yl)-piperidin-3-yl-methanone (racemic), MS: 387 (M+H)$^+$, mp: 130.5-136.7° C. (as hydrochloride); and (7-Benzenesulfo-nyl-2,3-dihydro-benzo[1,4]oxazin-4-yl)-piperidin-4-yl-methanone, MS: 387 (M+H)$^+$, mp: 294.8-299.1 ° C. (as hydrochloride).

Step 2:

1-(6-Benzenesulfonyl-2,3-dihydro-benzo[1,4]oxazin-4-yl)-2-(4,5-dihydro-1H-imidazol-2-yl)-ethanone

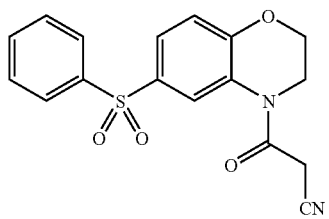

Step 2
1. HCl, EtOH
2. EDA

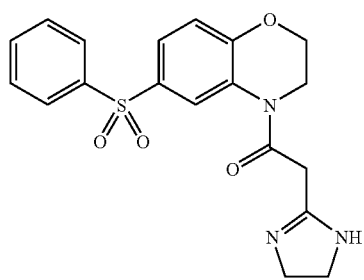

1-(6-Benzenesulfonyl-2,3-dihydro-benzo[1,4]oxazin-4-yl)-2-(4,5-dihydro-1H-imidazol-2-yl)-ethanone was prepared by treatment of 3-(6-benzenesulfonyl-2,3-dihydro-benzo[1,4]oxazin-4-yl)-3-oxo-propionitrile with HCl followed by ethylene diamine using the procedure described in Example 2. mp: 114-116.1° C.

Example 7

N-(7-Benzenesulfonyl-2,3-dihydro-benzo[1,4]oxazine-4-carbonyl)-guanidine

The synthetic procedures described in this Example were carried out according to the process shown in Scheme k.

SCHEME K

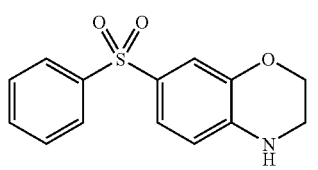

Step 1
COCl₂, TEA

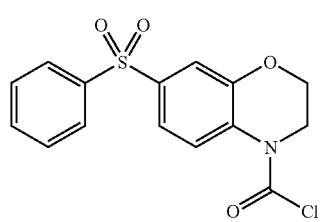

Step 2
Guanidine Carbonate, DIEA

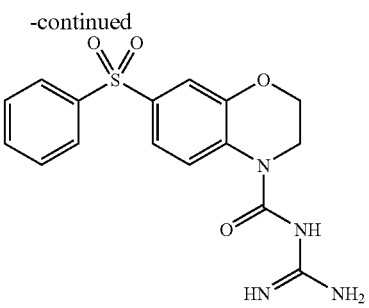

Step 1

7-Benzenesulfonyl-2,3-dihydro-benzo[1,4]oxazine-4-carbonyl chloride

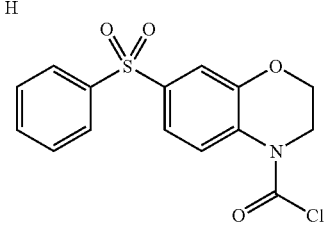

Step 1
COCl₂, TEA

To a solution of phosgene (1.44 mL of a 1.8 M solution in dichloromethane, 2.64 mmol) at 0° C. was added a solution of 7-benzenesulfonyl-3,4-dihydro-2H-benzo[1,4]oxazine (0.663 g., 2.4 mmol) in 3 mL dichloromethane followed by dropwise addition of triethylamine (0.361 mL, 2.6 mmol) over three minutes. The reaction was allowed to warm to room temperature and was stirred for an hour. The reaction mixture was then concentrated in vacuo, and then dissolved in 50 mL dichloromethane which was removed in vacuo. A suspension of the crude residue in 60 mL of 1:1 ethyl ether: hexanes was washed with 3 times with 50 mL of 6N aqueous hydrogen chloride. The organic fractions were dried over MgSO₄ and concentrated in vacuo to give 7-benzenesulfonyl-2,3-dihydro-benzo[1,4]oxazine-4-carbonyl chloride, which was used directly in the following step.

Step 2

N-(7-Benzenesulfonyl-2,3-dihydro-benzo[1,4]oxazine-4-carbonyl)-guanidine

Step 2
Guanidine Carbonate, DIEA

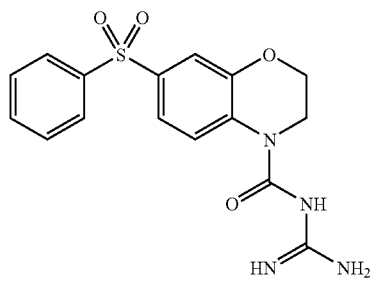

To a suspension of 7-benzenesulfonyl-2,3-dihydro-benzo[1,4]oxazine-4-carbonyl chloride (0.360 g., 1 mmol) in 20 mL acetonitrile, was added guanidine carbonate (0.180 g., 1 mmol), followed by the dropwise addition of N,N-diisopropyl ethylamine (0.523 mL, 3 mmol.) The reaction mixture was partitioned between 50 mL each of water and ethyl acetate. The organic fraction was washed with dilute aqueous hydrogen chloride followed by 50 mL water. The organic fraction was dried over sodium sulfate and concentrated in vacuo. The resulting white solid was dissolved in 20 mL refluxing dichloromethane. On cooling, white crystals formed, which were filtered and dried under vacuum to give 73 mg (21 %) of N-(7-benzenesulfonyl-2,3-dihydro-benzo[1,4]oxazine-4-carbonyl)-guanidine free base, which recrystallized from EtOH/HCl/Et₂O to provide the hydrochloride salt. MS: 361 (M+H)⁺, mp (as hydrochloride): 148.5-151.6° C.

Similarly prepared was N-(6-benzenesulfonyl-2,3-dihydro-benzo[1,4]oxazine-4-carbonyl)-guanidine, MS: 361 (M+H)⁺, mp (as hydrochloride): 61.2-67.3° C.

Example 8

7-Benzenesulfonyl-2,3-dihydro-benzo[1,4]oxazine-4-carboxylic acid (2-amino-ethyl)-amide The synthetic procedures described in this Example were carried out according to the process shown in Scheme L.

SCHEME L

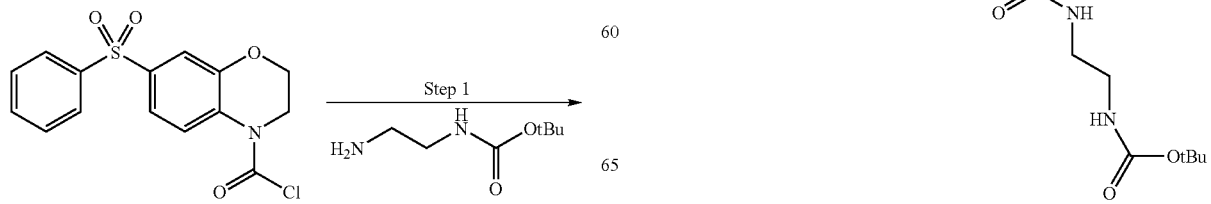

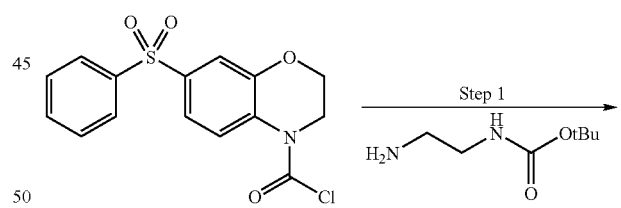

Step 1

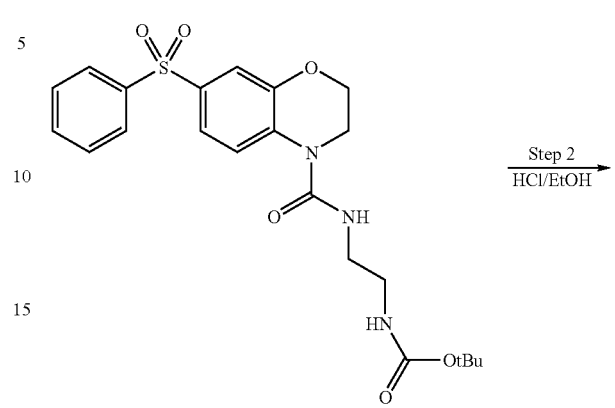

Step 1

2-[(7-Benzenesulfonyl-2,3-dihydro-benzo[1,4]oxazine-4-carbonyl)-amino]-ethyl}-carbamic acid tert-butyl ester To a suspension of 7-benzenesulfonyl-2,3-dihydro-benzo[1,4]oxazine-4-carbonyl chloride (0.129 g., 0.382 mmol) in 2 mL acetonitrile was added a solution of (2-amino-ethyl)-carbamic acid tert-butyl ester (0.123 g., 0.763 mmol) in 1 mL acetonitrile. The mixture was cooled to 0° C. and N,N-diisopropyl ethylamine (0.199 mL, 1.145 mmol) was added dropwise. The reaction mixture was stirred for 20 minutes, combined with 40 mL ethyl acetate, and washed with 50 mL water. The organic phase was dried over $Na_2SO_4$ and concentrated in vacuo. The residue was purified by flash chromatography (40-60% ethyl acetate in hexanes) to give 35 mg. of 2-[(7-benzenesulfonyl-2,3-dihydro-benzo[1,4]oxazine-4-carbonyl)-amino]-ethyl}-carbamic acid tert-butyl ester as a white solid.

Step 2

7-Benzenesulfonyl-2,3-dihydro-benzo[1,4]oxazine-4-carboxylic acid (2-amino-ethyl)-amide

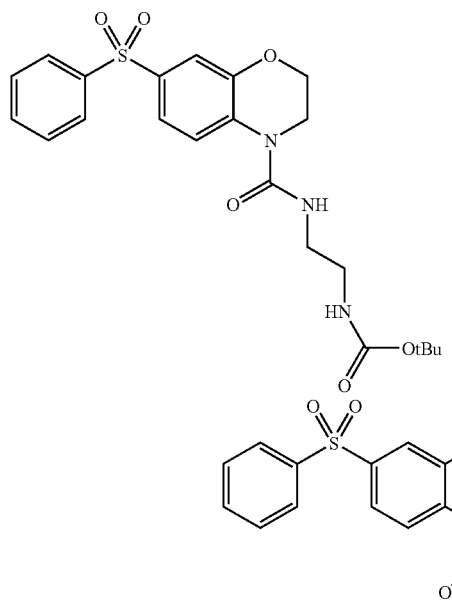

2-[(7-Benzenesulfonyl-2,3-dihydro-benzo[1,4]oxazine-4-carbonyl)-amino]-ethyl}-carbamic acid tert-butyl ester (38 mg) was dissolved in 1 mL ethanol and combined with 1 mL of 2N ethanolic HCl and refluxed for 30 minutes. Upon cooling, a white crystalline solid precipitated and filtration gave 25 mg. of 7-benzenesulfonyl-2,3-dihydro-benzo[1,4]oxazine-4-carboxylic acid (2-amino-ethyl)-amide hydrochloride. MS: 362 (M+H)$^+$, mp: 220.9-221.3° C.

Example 9

[3-(6-Benzenesulfonyl-2,3-dihydro-benzo[1,4]oxazin-4-yl)-propyl]-methyl-amine

The synthetic procedures described in this Example were carried out according to the process shown in Scheme M.

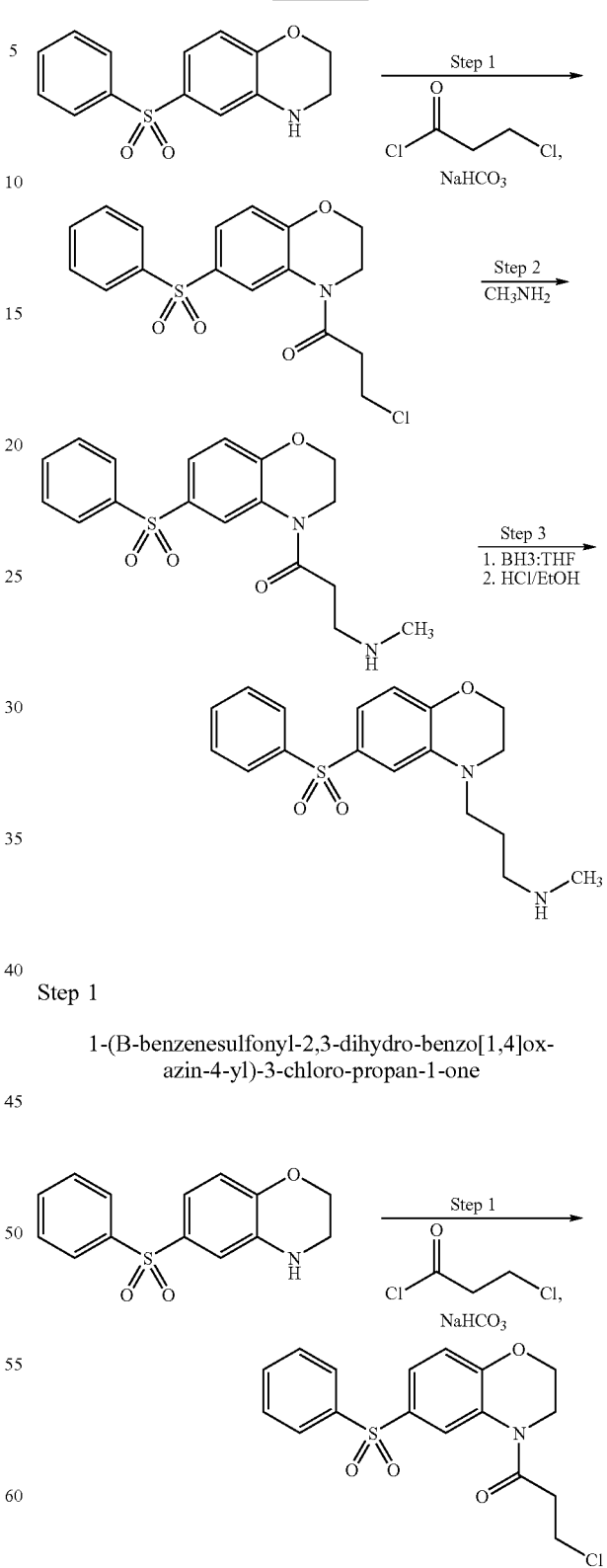

SCHEME M

Step 1

1-(B-benzenesulfonyl-2,3-dihydro-benzo[1,4]oxazin-4-yl)-3-chloro-propan-1-one

To a solution of 6-benzenesulfonyl-3,4-dihydro-2H-benzo[1,4]oxazine (0.530 g, 1.90 mmol) in 5 mL ethyl acetate was added 2 mL saturated aqueous sodium bicarbonate. The mixture was stirred rapidly and cooled to 0° C., and 3-chloro-propionyl chloride (0.219 mL, 2.30 mmol) was added dropwise over 2 minutes. Stirring was continued for 20 minutes, and 20 mL ethyl acetate was added to the reaction mixture. The organic phase was separated, dried over Na$_2$SO$_4$ and concentrated in vacuo to give 0.689 g (99%) of 1-(6-benzenesulfonyl-2,3-dihydro-benzo[1,4]oxazin-4-yl)-3-chloro-propan-1-one as an orange-white solid. MS: 367 (M+H)$^+$.

Step 2

1-(6-Benzenesulfonyl-2,3-dihydro-benzo[1,4]oxazin-4-yl)-3-methylamino-propan-1-one

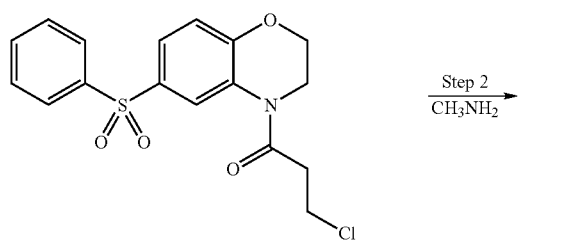

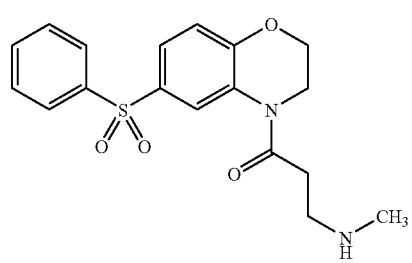

A solution of 1-(6-benzenesulfonyl-2,3-dihydro-benzo[1,4]oxazin-4-yl)-3-chloro-propan-1-one (0.100 g., 0.273 mmol) in 4 mL of 2 M methanolic H$_2$NMe was heated in a microwave reactor in a sealed reaction vessel at 80° C. for 2 minutes, then at 130° C. for 8 minutes. The reaction mixture was concentrated in vacuo and the residue was purified by flash chromatography (24:1:0.1 of CH$_2$Cl$_2$: MeOH:NH$_4$OH) to give 0.092 g (93%) of 1-(6-benzenesulfonyl-2,3-dihydro-benzo[1,4]oxazin-4-yl)-3-methylamino-propan-1-one as a clear oil. MS: 361 (M+H)$^+$, mp: 208.3-214.7° C. (as hydrochloride).

The following compounds were prepared in a similar fashion using the appropriate alkyl chloride and amine:

1-(6-Benzenesulfonyl-2,3-dihydro-benzo[1,4]oxazin-4-yl)-3-dimethylamino-propan-1-one, MS: 375, mp: 81.0-82.0° C. (as hydrochloride);

1-(6-Benzenesulfonyl-2,3-dihydro-benzo[1,4]oxazin-4-yl)-2-dimethylamino-ethanone, MS: 361, mp: 199.0-203.0° C. (as hydrochloride); and 1-(6-Benzenesulfonyl-2,3-dihydro-benzo[1,4]oxazin-4-yl)-2-methylamino-ethanone, MS: 347, mp: 233.0-235.5° C. (as hydrochloride).

Step 3

[3-(6-Benzenesulfonyl-2,3-dihydro-benzo[1,4]oxazin-4-yl)-propyl]-methyl-amine

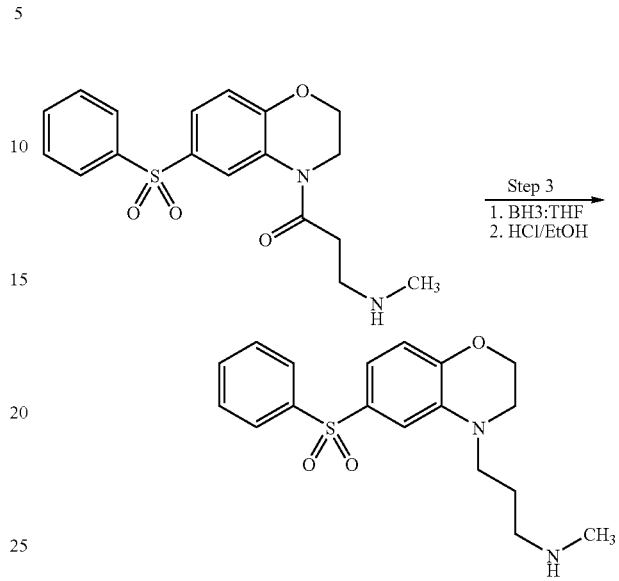

To 1 mL of freshly distilled THF was added 1-(7-benzenesulfonyl-2,3-dihydro-benzo[1,4]oxazin-4-yl)-3-methylamino-propan-1-one (0.075 g, 0.210 mmol) and the resulting solution was cooled to 0° C. Borane:THF complex (0.315 mL of a 1 M solution, 0.315 mmol) was added dropwise over 2 minutes, during which offgassing was observed. The solution was warmed to reflux for 6 hours with stirring and then cooled to room temperature. Ethanolic hydrogen chloride (0.750 mL of a 2N solution, 1.5 mmol) was added dropwise accompanied by vigorous offgassing. The reaction mixture was refluxed for 2 hours at which time a white solid was observed in the solution. To the reaction mixture was added 2 mL diethyl ether and the solid was filtered and dried overnight under reduced pressure to give 0.045 g. of [3-(7-benzenesulfonyl-2,3-dihydro-benzo[1,4]oxazin-4-yl)-propyl]-methyl-amine hydrochloride as a fluffy white solid. MS: 347 (M+H)$^+$, mp: 188.3-193.2° C. (as hydrochloride salt).

The following compounds were prepared in a similar fashion using the appropriate amide:

[3-(6-Benzenesulfonyl-2,3-dihydro-benzo[1,4]oxazin-4-yl)-propyl]-methyl-amine, MS: 347 (M+H)$^+$, mp: 235.1-236.9° C. (as hydrochloride salt);

4-Azetidin-3-ylmethyl-7-benzenesulfonyl-3,4-dihydro-2H-benzo[1,4]oxazine, MS: 345 (M+H)$^+$, mp: 194.9-196.0° C. (as hydrochloride salt); and 7-Benzenesulfonyl-4-(2-imidazol-1-yl-ethyl)-3,4-dihydro-2H-benzo[1,4]oxazine, MS: 370 (M+H)$^+$, mp: 61.5-64.4° C. (as hydrochloride salt).

Example 10

1-(7-Benzenesulfonyl-2,3-dihydro-benzo[1,4]oxazin-4-yl)-2-imidazol-1-yl-ethanone The synthetic procedures described in this Example were carried out according to the process shown in Scheme N.

SCHEME N

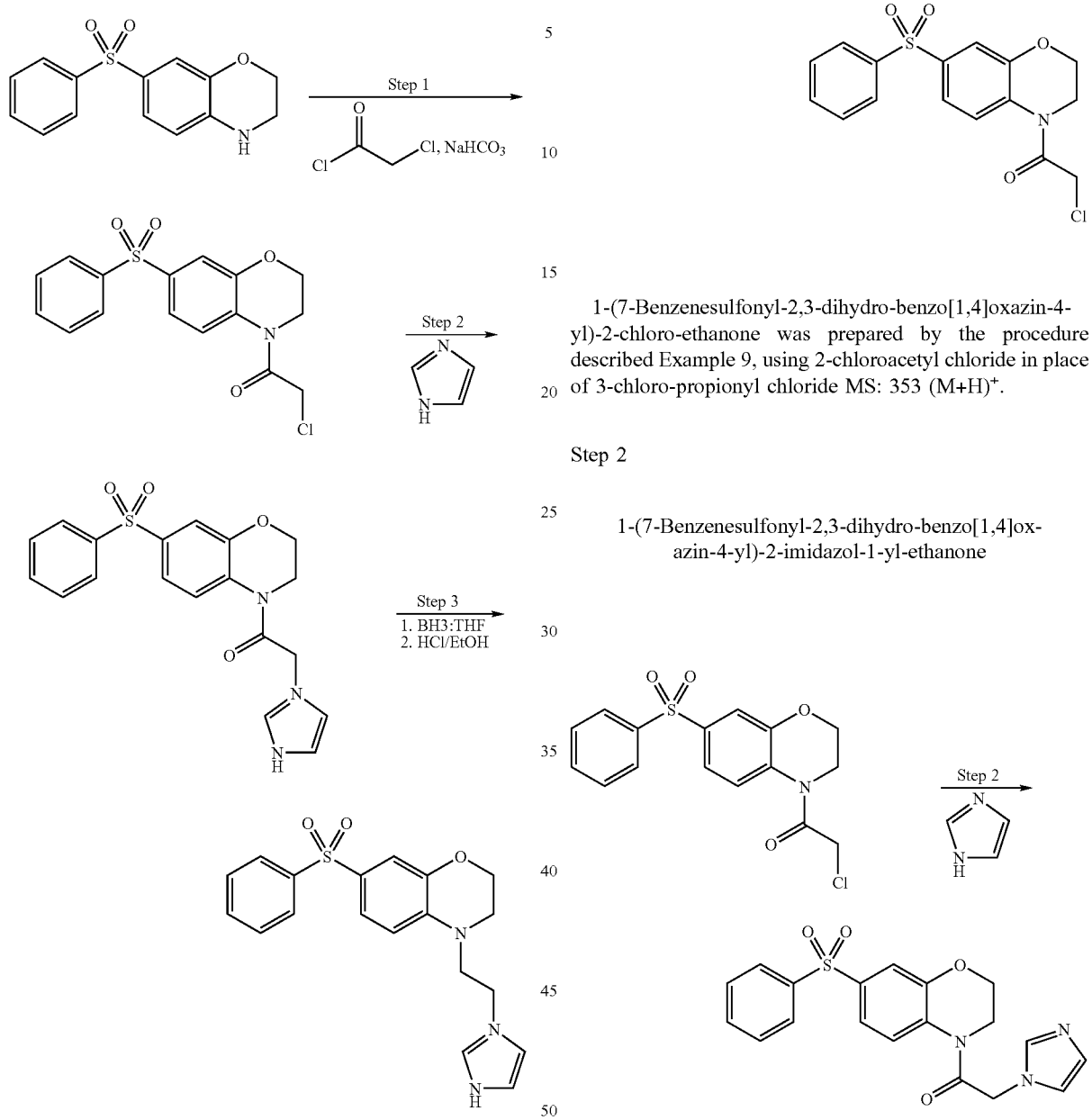

Step 1

1-(7-Benzenesulfonyl-2,3-dihydro-benzo[1,4]oxazin-4-yl)-2-chloro-ethanone

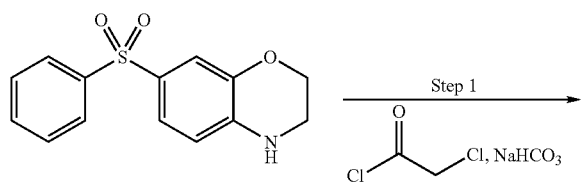

1-(7-Benzenesulfonyl-2,3-dihydro-benzo[1,4]oxazin-4-yl)-2-chloro-ethanone was prepared by the procedure described Example 9, using 2-chloroacetyl chloride in place of 3-chloro-propionyl chloride MS: 353 (M+H)⁺.

Step 2

1-(7-Benzenesulfonyl-2,3-dihydro-benzo[1,4]oxazin-4-yl)-2-imidazol-1-yl-ethanone To a solution of 1-(7-benzenesulfonyl-2,3-dihydro-benzo[1,4]oxazin-4-yl)-2-chloro-ethanone (0.216 g., 0.614 mmol) in 2 mL acetonitrile was added potassium carbonate (0.101 g., 0.737 mmol), imidazole (0.209 g., 3.07 mmol) and sodium iodide (2 mg, cat.), and the resulting suspension was refluxed for 2 hours. The reaction mixture was added to 100 mL ethyl acetate, and the inorganic components extracted three times with 50 mL water. The aqueous fraction was extracted twice with 50 mL ethyl acetate, and the combined organic fractions were dried over sodium sulfate and concentrated in vacuo. The crude solid was recrystallized from 3 mL dichloromethane to give 100 mg (42%) of 1-(7-benzenesulfonyl-2,3-dihydro-benzo[1,4]oxazin-4-yl)-2-imidazol-1-yl-ethanone as a white solid. MS: 385 (M+H)⁺.

Step 3

7-Benzenesulfonyl-4-[2-(3H-imidazol-1-yl)-ethyl]-3,4-dihydro-2H-benzo[1,4]oxazine

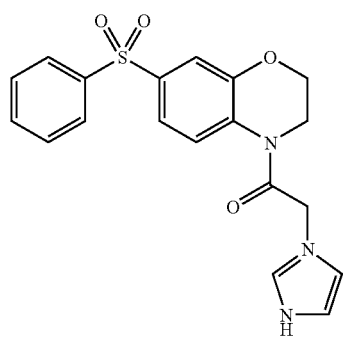

7-Benzenesulfonyl-4-[2-(3H-imidazol-1-yl)-ethyl]-3,4-dihydro-2H-benzo[1,4]oxazine was prepared by reducing 1-(7-benzenesulfonyl-2,3-dihydro-benzo[1,4]oxazin-4-yl)-2-imidazol-1-yl-ethanone with $BH_3$:THF using the procedure of Example 9. mp: 61.5-64.4° C.

Example 11

7-Benzenesulfonyl-4-piperidin-4-yl-3,4-dihydro-2H-benzo[1,4]oxazine

The synthetic procedures described in this Example were carried out according to the process shown in Scheme O.

SCHEME O

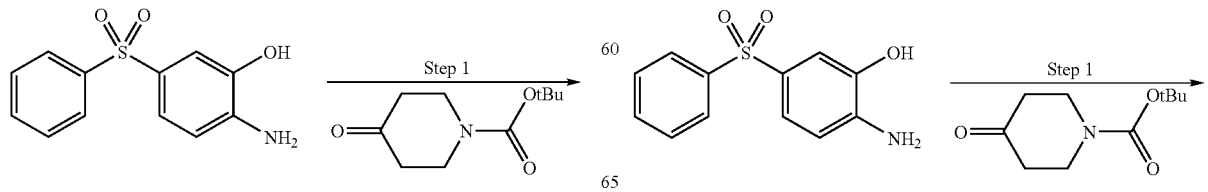

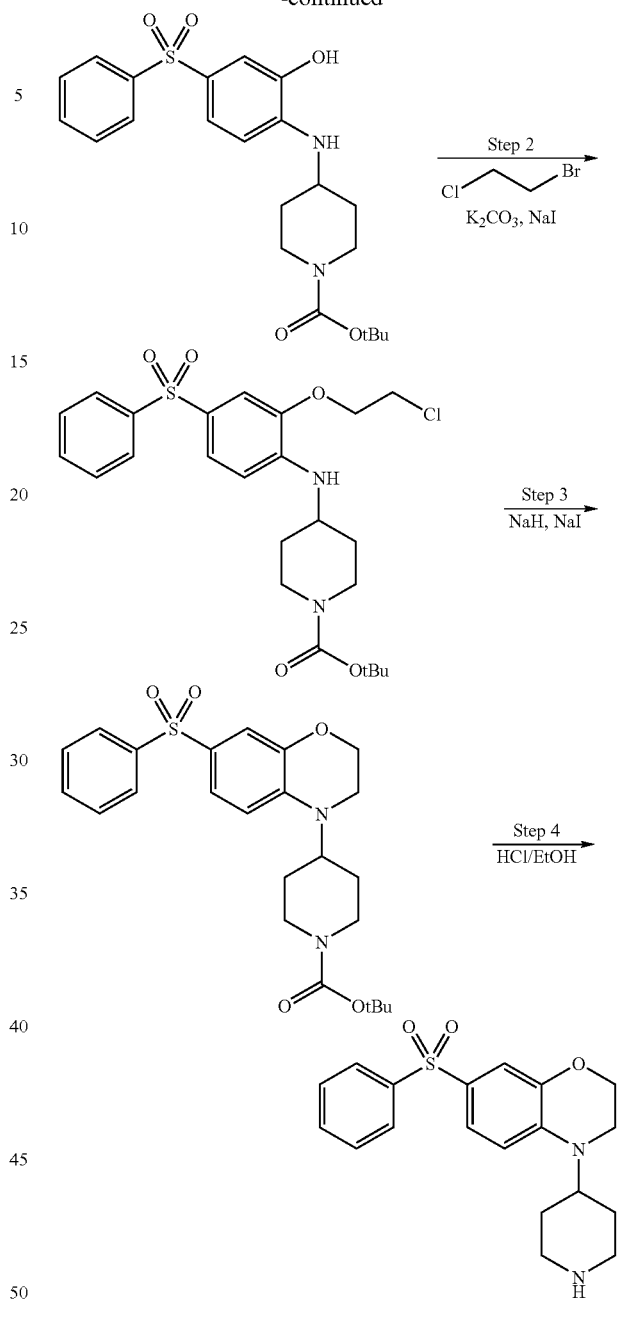

Step 1

4-(4-Benzenesulfonyl-2-hydroxy-phenylamino)-piperidine-1-carboxylic acid tert-butyl ester -continued

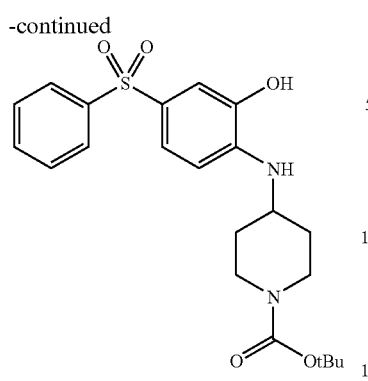

To a solution of 2-amino-5-benzenesulfonyl-phenol (1.00 g., 4.016 mmol) in 20 mL dichlormethane was added 4-oxo-piperidine-1-carboxylic acid tert-butyl ester (0.880 g, 4.418 mmol) followed by sodium triacetoxyborohydride (1.78 g, 8.43 mmol) and the resulting suspension was stirred at room temperature under nitrogen for 24 hours. The reaction mixture was washed twice with 50 mL water, once with 50 mL brine, then dried over sodium sulfate and concentrated in vacuo. The resulting crude solid was purified by flash chromatography (20-30% ethyl acetate in hexanes) to give 1.823 g (4.53 mmol, 94%) of 4-(4-benzenesulfonyl-2-hydroxy-phenylamino)-piperidine-1-carboxylic acid tert-butyl ester as a foam. MS: 333 (M–CO$_2^t$Bu+H)$^+$, 377 (M–$^t$Bu+H)$^+$.

Step 2

4-[4-Benzenesulfonyl-2-(2-chloro-ethoxy)-phenylamino]-piperidine-1-carboxylic acid tert-butyl ester

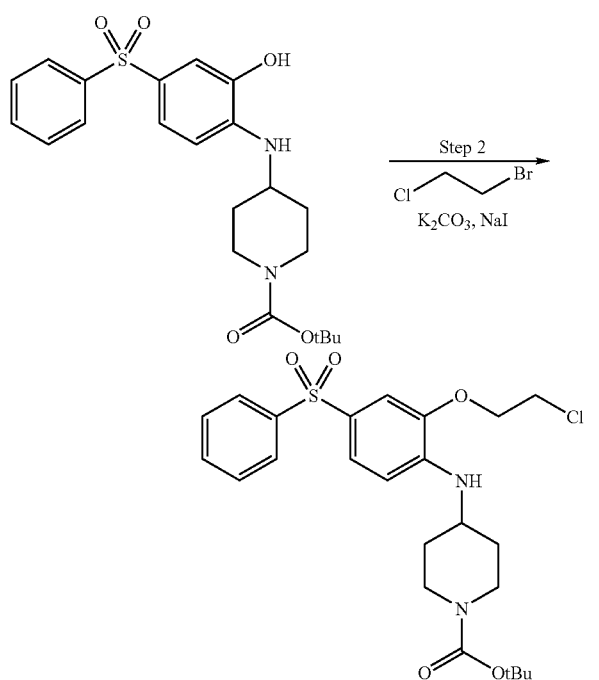

To a solution of 4-(4-benzenesulfonyl-2-hydroxy-phenylamino)-piperidine-1-carboxylic acid tert-butyl ester (0.192 g., 0.444 mmol) in 1 mL acetonitrile is added potassium carbonate (0.245 g., 1.776 mmol) and then 1-bromo-2-chloro-ethane (0.044 mL, 0.535 mmol) dropwise. The suspension is refluxed under nitrogen for 3 hours, at which time is added 1-bromo-2-chloro-ethane (0.044 mL, 0.535 mmol) dropwise. Reflux is continued for another 1.5 hours. The reaction mixture is concentrated in vacuo and the resulting oil is dissolved in 75 mL ethyl acetate, washed with 2×50 mL water and 50 mL brine, then dried over sodium sulfate and concentrated in vacuo. The resulting crude oil is purified by flash chromatography (10% -30% ethyl acetate in hexanes) to give 0.175 g (0.35 mmol, 80%) of 4-[4-benzenesulfonyl-2-(2-chloro-ethoxy)-phenylamino]-piperidine-1-carboxylic acid tert-butyl ester as a clear oil. MS: 439 (M–$^t$Bu+H)$^+$.

Step 3

4-(7-Benzenesulfonyl-2,3-dihydro-benzo[1,4]oxazin-4-yl)-piperidine-1-carboxylic acid tert-butyl ester

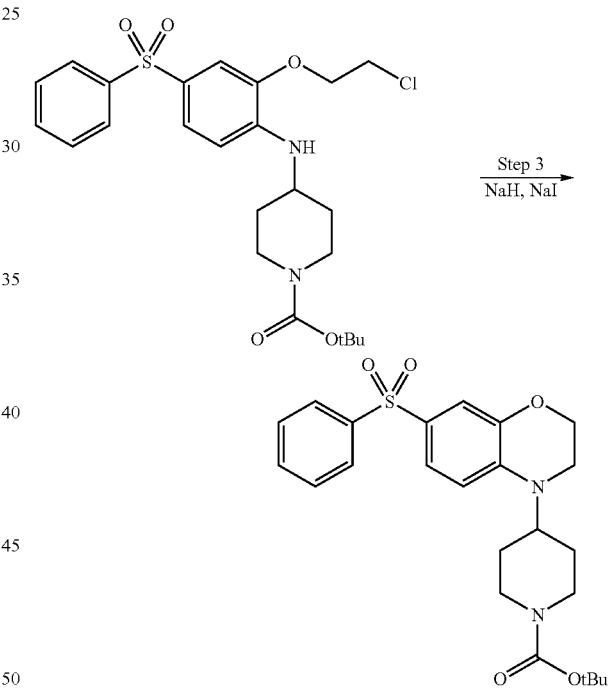

To a solution of 4-[4-benzenesulfonyl-2-(2-chloroethoxy)-phenylamino]-piperidine-1-carboxylic acid tert-butyl ester (0.175 g, 0.354 mmol) in 0.500 mL anhydrous DMF was added sodium iodide (2.0 mg, cat) followed by sodium hydride (17 mg. of a 60% dispersion in mineral oil, 0.424 mmol) in 3 portions. The reaction mixture was stirred at room temperature for 2 hours, added to 50 mL water, and then extracted twice with 50 mL ethyl acetate. The organic fraction was washed with 50 mL brine, dried over sodium sulfate, then concentrated in vacuo. The resulting crude oil was purified by flash chromatography (10%-40% ethyl acetate in hexanes) to give 0.111 g (0.242 mmol, 68%) of 4-(7-benzenesulfonyl-2,3-dihydro-benzo[1,4]oxazin-4-yl)-piperidine-1-carboxylic acid tert-butyl ester.

Step 4

7-Benzenesulfonyl-4-piperidin-4-yl-3,4-dihydro-2H-benzo[1,4]oxazine

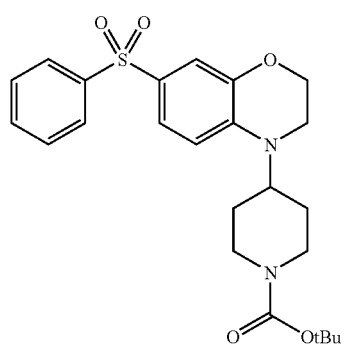

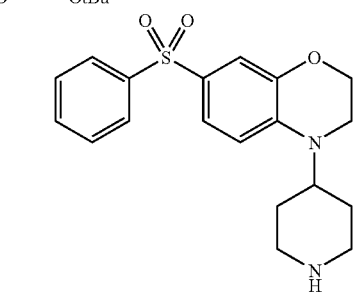

4-(7-Benzenesulfonyl-2,3-dihydro-benzo[1,4]oxazin-4-yl)-piperidine-1-carboxylic acid tert-butyl ester (0.111 g, 0.242 mmol) was dissolved in 5 mL ethyl alcohol and brought to reflux. To the solution was added ethanolic hydrogen chloride (2 mL of a 2N solution, 4.0 mmol) and reflux continued for 0.5 hours. The solution is concentrated to 1 mL and ethyl ether (10 mL) is added until a white precipitate is observed. Filtration gave 0.085 g (quantitative) of 7-benzenesulfonyl-4-piperidin-4-yl-3,4-dihydro-2H-benzo[1,4]oxazine hydrochloride as a white powder. MS: 359 (M+H)+, mp: 251.9-253.2° C.

Similarly prepared using 4-[5-benzenesulfonyl-2-(2-bromo-ethoxy)-phenylamino]-piperidine-1-carboxylic acid tert-butyl ester, was 6-Benzenesulfonyl-4-piperidin-4-yl-3,4-dihydro-2H-benzo[1,4]oxazine, MS: 359 (M+H)+, mp: 147.0-149.8° C.

Example 12

7-Benzenesulfonyl-4-pyrrolidin-3-yl-3,4-dihydro-2H-benzo[1,4]oxazine

The synthetic procedures described in this Example were carried out according to the process shown in Scheme P.

SCHEME P

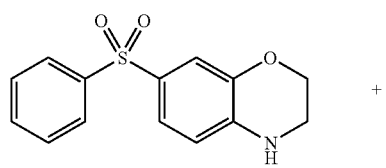

-continued

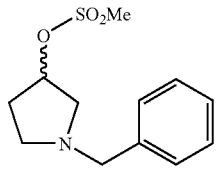

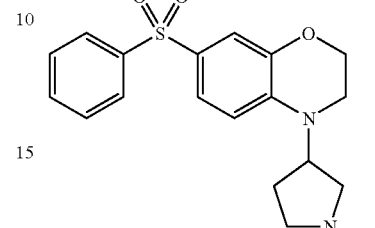

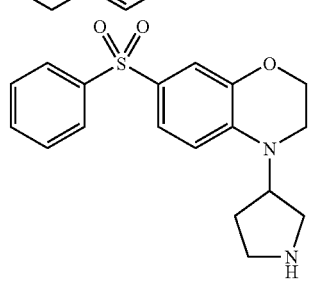

Step 1

7-Benzenesulfonyl-4-(1-benzyl-pyrrolidin-3-yl)-3,4-dihydro-2H-benzo[1,4]oxazine

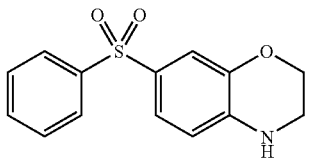

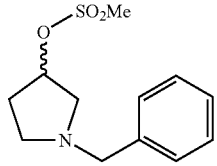

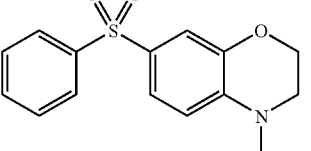

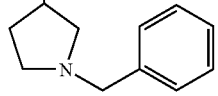

The methanesulfonic acid 1-benzyl-pyrrolidin-3-yl ester used in this example was prepared using the procedure described by Ahn et al., "N-Substituted 3-Arylpyrrolidines: Potent and Selective Ligands at the Serotonin 1A Receptor", Bioorganic and Medicinal Chemistry Letters, 9(10), 1999, 1379-1384.

To a suspension of sodium hydride (0.033 g. of a 60% dispersion in mineral oil, 0.834 mmol) in 3 mL dimethylformamide was added portionwise 7-benzenesulfonyl-3,4-dihydro-2H-benzo[1,4]oxazine (0.200 g, 0.726 mmol), and the resulting suspension was stirred at room temperature for 10 minutes. Racemic methanesulfonic acid 1-benzyl-pyrrolidin-3-yl ester (0.259 g., 1.018 mmol) was added dropwise and the reaction mixture was heated to 65° C. for 21 hours. The reaction mixture was then poured into 100 mL water, and extracted three times with 50 mL ethyl acetate. The organic fraction was washed twice with 50 mL 10% aq. hydrogen chloride and once with 50 mL saturated sodium bicarbonate. The organic fraction was then dried over sodium sulfate and concentrated in vacuo. The crude product was purified by flash chromatography (2%-5% methanol in dichlormethane) to give 0.127 g (0.292 mmol, 40%) of 7-benzenesulfonyl-4-(1-benzyl-pyrrolidin-3-yl)-3,4-dihydro-2H-benzo[1,4]oxazine as a red oil. MS: 474 (M+ACN)$^+$.

Step 2

7-Benzenesulfonyl-4-pyrrolidin-3-yl-3,4-dihydro-2H-benzo[1,4]oxazine

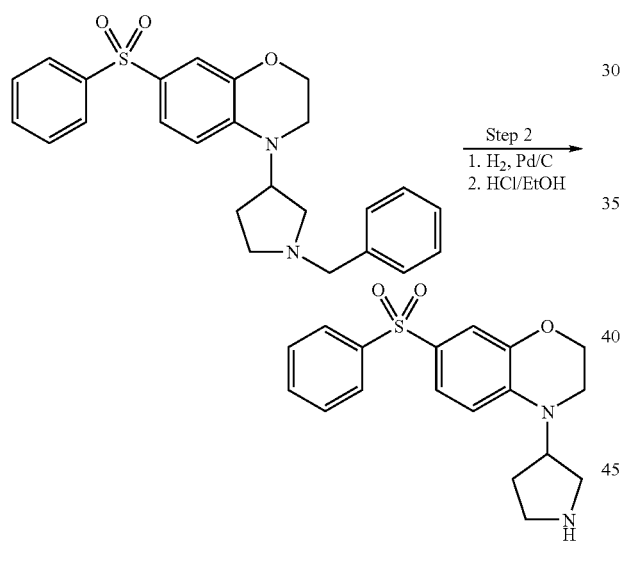

7-Benzenesulfonyl-4-(1-benzyl-pyrrolidin-3-yl)-3,4-dihydro-2H-benzo[1,4]oxazine (0.127 g, 0.292 mmol) was dissolved in 15 mL ethanol and this solution was added to a flask containing 35 mg of 5% palladium on charcoal, followed by 3 drops of glacial acetic acid. The system was purged with hydrogen gas and stirring was continued for 24 hours under 1 atm. of hydrogen gas. The reaction mixture was filtered through celite, the filtrate concentrated in vacuo, and the resulting solid purified by flash (6:0.4:0.04 of CH$_2$Cl$_2$:MeOH:NH$_4$OH) to give 45 mg of 7-benzenesulfonyl-4-pyrrolidin-3-yl-3,4-dihydro-2H-benzo[1,4]oxazine as free base. This solid was dissolved in 1 mL methanol and combined with 0.5 mL of 2N ethanolic hydrogen chloride and the resulting solution is concentrated in vacuo and subjected to a vacuum of 0.3 Torr for 2 hours to give a foam which was triturated twice with 50 mL ethyl ether to give, after drying under reduced pressure, 25 mg (0.07 mmol, 25%) of 7-benzenesulfonyl-4-pyrrolidin-3-yl-3,4-dihydro-2H-benzo[1,4]oxazine hydrochloride as a tan solid. MS: 345 (M+H)$^+$, mp: 122.8-127.6° C.

Example 13

7-Benzenesulfonyl-2,2-dimethyl-4-piperidin-4-yl-3,4-dihydro-2H-benzo[1,4]oxazine The synthetic procedures described in this Example were carried out according to the process shown in Scheme Q.

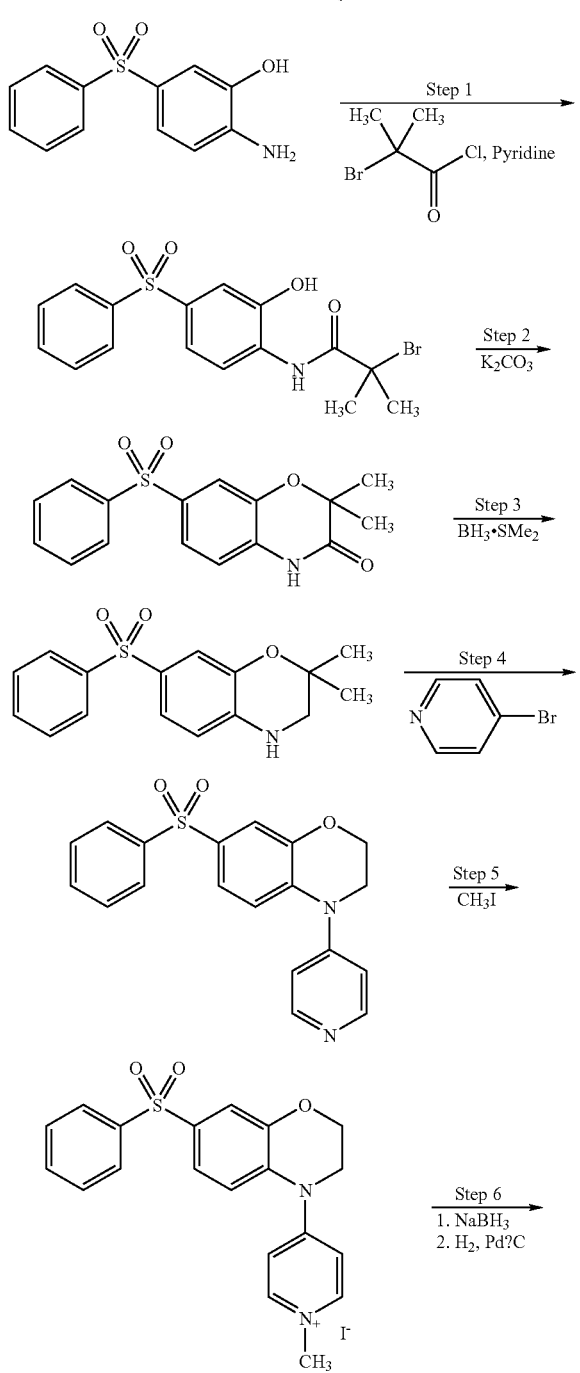

77

-continued

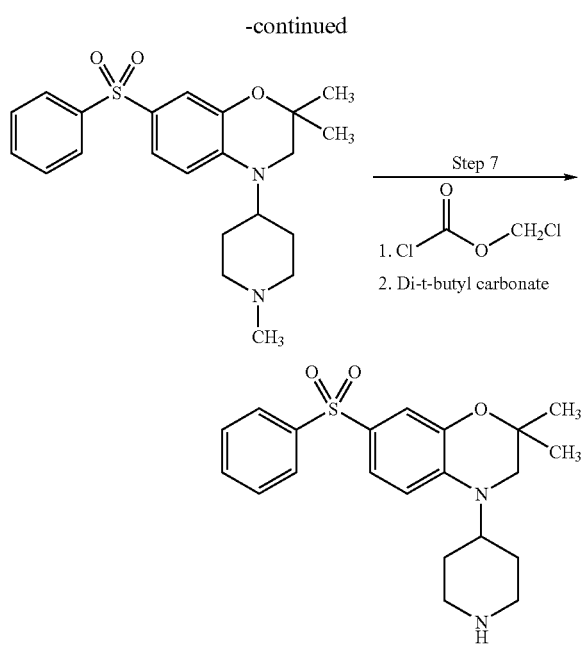

Step 1

7-Benzenesulfonyl-2,2-dimethyl-4H-benzo[1,4]ox-azin-3-one

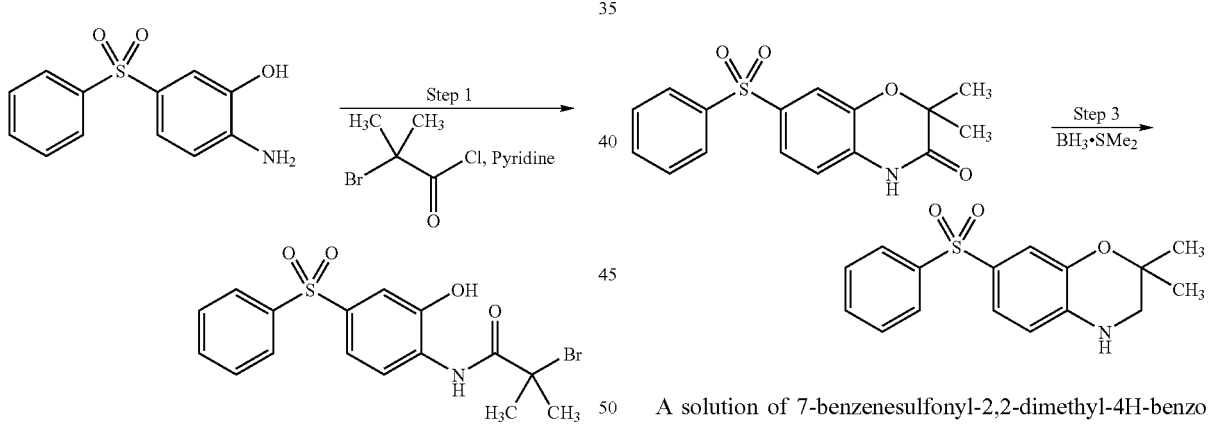

To a solution of 2-amino-5-benzenesulfonyl-phenol (1.06 g., 4.26 mmol) in 8 mL ethyl acetate was added pyridine (0.345 mL, 4.26 mmol). The solution was cooled to 0° C. and 2-bromo-2-methyl-propionyl chloride (0.553 mL, 4.47 mmol) was added dropwise and stirring was continuted for 2 hours. The reaction mixture was diluted with 50 mL ethyl acetate and washed with 50 mL 10% aqueous hydrogen chloride, 50 mL saturated aqueous sodium bicarbonate, 50 mL water, then 50 mL brine. The organic phase was dried over sodium sulfate and concentrated in vacuo to yield 5-benzenesulfonyl-2-(2-bromo-2-methyl-propylamino)-phenol as a crude oil, which was used directly in the following step.

78

Step 2

7-Benzenesulfonyl-2,2-dimethyl-4H-benzo[1,4]ox-azin-3-one

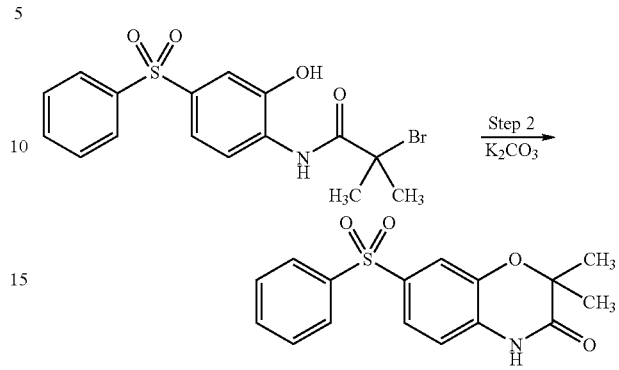

The crude 5-benzenesulfonyl-2-(2-bromo-2-methyl-propylamino)-phenol from step 1 was dissolved in 10 mL DMF and potassium carbonate (0.565 g., 4.096 mmol) was added. The reaction mixture was heated to 80° C. with stirring for 2 hours, then cooled to room temperature and poured onto 100 g of ice in 150 mL 10% aqueous hydrogen chloride. The resulting solid was filtered and dried under vacuum for 18 hours to give 0.570 g (1.79 mmol) of 7-benzenesulfonyl-2,2-dimethyl-4H-benzo[1,4]oxazin-3-one. MS: 316 (M−H)⁻.

Step 3

7-Benzenesulfonyl-2,2-dimethyl-3,4-dihydro-2H-benzo[1,4]oxazine

A solution of 7-benzenesulfonyl-2,2-dimethyl-4H-benzo [1,4]oxazin-3-one (0.570 g., 1.79 mmol) in 10 mL freshly distilled THF was cooled to 0° C., and borane-THF complex (5.39 mL of a 1 M solution in THF, 5.39 mmol) was added dropwise over 2 minutes. The resulting solution was warmed to reflux and stirred for 1 hour. Ethanolic hydrogen chloride (4 mL of 2 N solution, 8 mmol) was then added dropwise and the reaction was heated at reflux for an additional hour. The reaction mixture was cooled to room temperature and added to a mixture of 100 mL each ethyl acetate and 10% aqueous sodium bicarbonate. Potassium carbonate was added until the pH of the aqueous phase was roughly 7. The organic layer was separated, washed with 50 mL water and 50 mL brine, dried over sodium sulfate and concentrated in vacuo. The resulting crude oil was purified by flash chromatography (10 to 45% ethyl acetate in hexanes) to give 520 mg (94%) of 7-benzenesulfonyl-2,2-dimethyl-3,4-dihydro-2H-benzo[1,4]oxazine as a white powder. MS: 304 (M+H)⁺.

Step 4

7-Benzenesulfonyl-2,2-dimethyl-4-pyridin-4-yl-3,4-dihydro-2H-benzo[1,4]oxazine

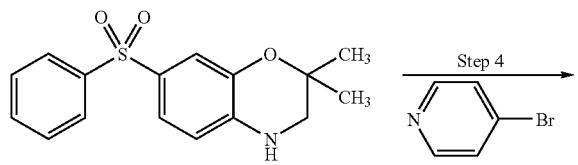

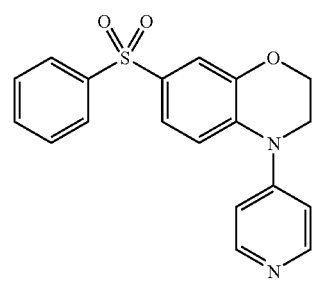

A mixture of 7-benzenesulfonyl-2,2-dimethyl-3,4-dihydro-2H-benzo[1,4]oxazine (0.257 g., 0.847 mmol) and 4-bromopyridinium chloride (0.658 g., 3.388 mmol) was heated without solvent at 185° C. for 45 minutes. The reaction mixture was cooled to room temperature, suspended in 5 mL dichloromethane and concentrated in vacuo. The resulting crude oil was dissolved in a mixture of 50 mL ethyl acetate and 50 mL water. The aqueous layer was made strongly basic with 50 mL of 2N aqueous potassium carbonate, and the phases were separated. The organic phase was washed with twice with 50 mL water and once with 50 mL brine, dried over sodium sulfate and concentrated in vacuo. The resulting crude oil was purified by flash chromatography (3% methanol in dichloromethane) to give 161 mg (54%) of 7-benzenesulfonyl-2,2-dimethyl-4-pyridin-4-yl-3,4-dihydro-2H-benzo[1,4]oxazine as a foam. MS: 381 (M+H)+, mp: 112.7-120.4° C. (as hydrochloride salt).

Step 5

4-(7-Benzenesulfonyl-2,2-dimethyl-2,3-dihydro-benzo[1,4]oxazin-4-yl)-1-methyl-pyridinium Iodide

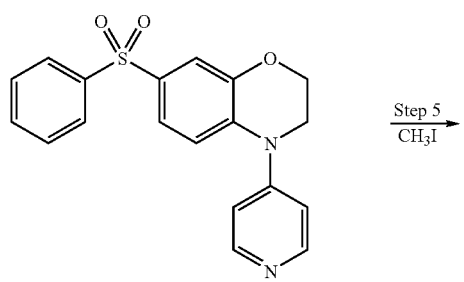

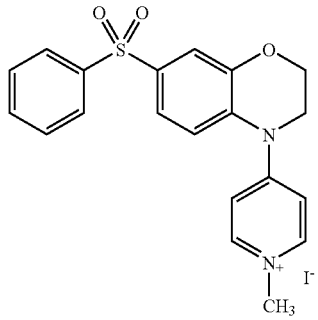

To a solution of 7-benzenesulfonyl-2,2-dimethyl-4-pyridin-4-yl-3,4-dihydro-2H-benzo[1,4]oxazine (0.187 g., 0.492 mmol) in 9.5 mL acetonitrile was added methyl iodide (0.153 mL, 2.461 mmol). The solution was refluxed for 10 minutes, cooled to 40° C. and methyl iodide (0.153 mL, 2.461 mmol) was added. The resulting solution was stirred at 35° C. for one hour, concentrated in vacuo, and subjected to a vacuum of 0.5 torr for 10 minutes to give 237 mg. of 4-(7-benzenesulfonyl-2,2-dimethyl-2,3-dihydro-benzo[1,4]oxazin-4-yl)-1-methyl-pyridinium iodide as a glassy yellow oil. MS: 395, M+.

Step 6

7-Benzenesulfonyl-2,2-dimethyl-4-(1-methyl-piperidin-4-yl)-3,4-dihydro-2H-benzo[1,4]oxazine

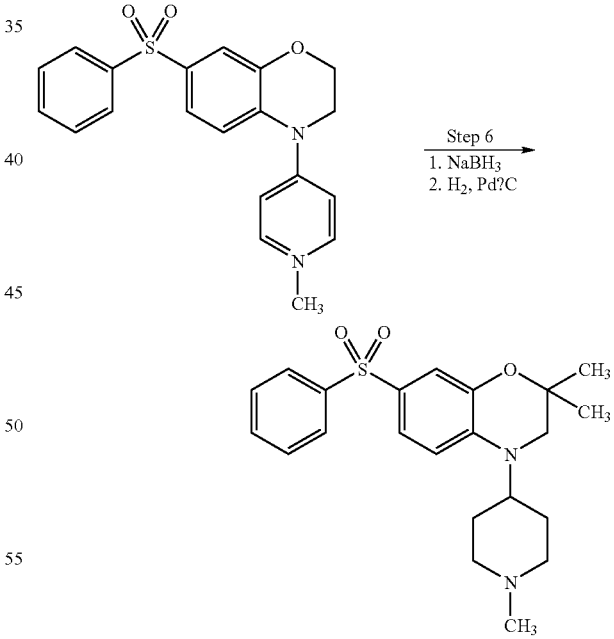

A solution of 4-(7-benzenesulfonyl-2,2-dimethyl-2,3-dihydro-benzo[1,4]oxazin-4-yl)-1-methyl-pyridinium iodide (0.237 g., 0.452 mmol) in 10 mL methanol was added to a suspension of sodium borohydride (0.085 g., 2.260 mmol) in 10 mL methanol at 0C. The reaction was stirred at 0° C. for 3 hours, then stirred for 18 hours at room temperature. The reaction mixture was concentrated in vacuo and the resulting crude solid was dissolved in a mixture of 50 mL water and 50 mL ethyl acetate. The organic phase was washed twice with 50 mL ethyl acetate, and the combined organic phase was dried over sodium sulfate and concentrated in vacuo to give 187 mg. of a yellow foam. This foam was dissolved in 20 mL ethanol and added to 25 mg. of a 5% dispersion of palladium metal on charcoal suspended in 5 mL ethanol. The suspension was purged with hydrogen gas and maintained at a pressure of 55 psi for 48 hours. The reaction mixture was filtered through celite, concentrated in vacuo and purified by flash chromatography (12:1:0.1 $CH_2Cl_2$:MeOH:$NH_4OH$) to give 114 mg (63%) of 7-benzenesulfonyl-2,2-dimethyl-4-(1-methyl-piperidin-4-yl)-3,4-dihydro-2H-benzo[1,4]oxazine as a clear oil. MS: 401 $(M+H)^+$.

Step 7

7-Benzenesulfonyl-2,2-dimethyl-4-piperidin-4-yl-3,4-dihydro-2H-benzo[1,4]oxazine

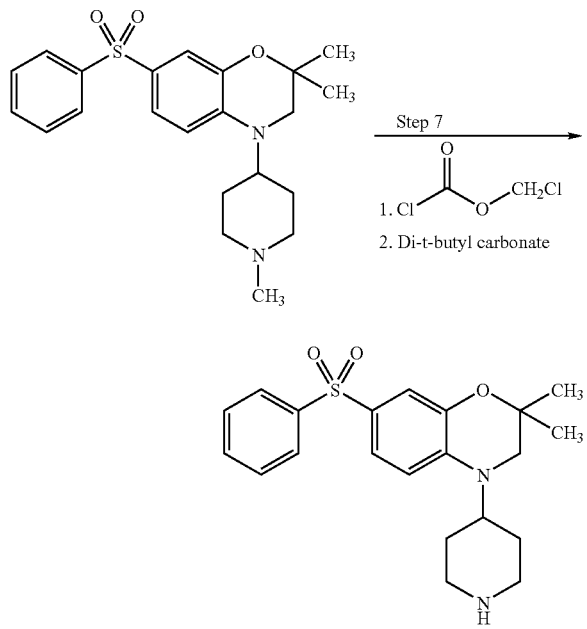

A solution of 7-benzenesulfonyl-2,2-dimethyl-4-(1-methyl-piperidin-4-yl)-3,4-dihydro-2H-benzo[1,4]oxazine (0.119 g., 0.298 mmol) in 3 mL dichloroethane was cooled to 0° C. and α-chloroethyl chloroformate (0.033 mL, 0.312 mmol) was added dropwise with stirring over 1 minute. The reaction mixture was refluxed for 18 hours, concentrated in vacuo, and the residue dissolved in 20 mL methanol and refluxed for 1 hour. The reaction mixture was concentrated in vacuo and a vacuum of 0.5 Torr was applied for 30 minutes. The resulting residue was dissolved in 35 mL THF, to which was added di-tert-butyldicarbonate (0.065 g., 0.300 mmol) and the reaction mixture was stirred for 72 hours at room temperature. The reaction mixture was then concentrated in vacuo and purified by flash chromatography (15% ethyl acetate in hexanes) to afford 0.087 g (75%) of 7-benzenesulfonyl-2,2-dimethyl-4-piperidin-4-yl-3,4-dihydro-2H-benzo[1,4]oxazine as a waxy solid. MS: 387, mp: 284.9-296.3° C. (as hydrochloride salt).

Example 14

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2- 2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH.

The nasal spray formulations may be delivered via a nasal spray metered pump typically delivering about 50-100 microliters of formulation per actuation. A typical dosing schedule is 2-4 sprays every 4-12 hours.

Example 15

Radioligand Binding Studies

This example illustrates in vitro radioligand binding studies of compound of formula I.

The binding activity of compounds of this invention in vitro was determined as follows. Duplicate determinations of 5-HT$_6$ ligand affinity were made by competing for binding of [$^3$H]LSD in cell membranes derived from HEK293 cells stably expressing recombinant human 5-HT$_6$ receptor. Duplicate determinations of 5-HT$_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably expressing recombinant human 5-HT$_{2A}$ receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J Pharmacol. Jun;115(4): 622-8 (1995).

For estimation of affinity at the 5-HT$_6$ receptor, all determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. For estimation of affinity at the 5-HT$_{2A}$ receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-HT$_6$) or 60 min. at 32° C. (for 5-HT$_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{B\text{max} - \text{basal}}{1 + 10^{-Hill(\log[ligand] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, compounds of Formula I were tested and found to be selective 5-HT6 antagonists. For example, the compound 7-benzenesulfonyl-4-piperidin-4-yl-3,4-dihydro-2H-benzo[1,4]oxazine exhibted a pKi of approximately 9.98 for the 5-HT6 receptor, and a pKi of approximately 8.09 for the 5-HT2A receptor.

Example 16

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

The invention claimed is:
1. A compound of the formula I:

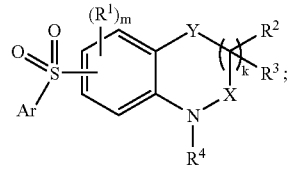

or a pharmaceutically acceptable salt or solvate thereof, wherein:
Ar is optionally substituted phenyl or optionally substituted naphthyl;
X is —CH$_2$— or C=O;
Y is O;
k is 1;
m is from 0 to 3;
each R$^1$ is independently halo, alkyl, haloalkyl, heteroalkyl, alkoxy, cyano, —S(O)$_q$—R$^b$, —C(=O)—NR$^c$R$^d$, —SO$_2$—NR$^c$R$^d$, N(R$^e$)—C(=O)—R$^f$, or —C(=O)—R$^f$, where q is from 0 to 2, R$^b$, R$^c$, R$^d$ and R$^e$ each independently is hydrogen or alkyl, and R$^f$ is hydrogen, alkyl, alkoxy or hydroxy;
R$^2$ and R$^3$ each independently is hydrogen or alkyl, or R$^2$ and R$^3$ together with the carbon atom to which they are attached may form a carbocyclic ring of four to six members;
R$^4$ is:

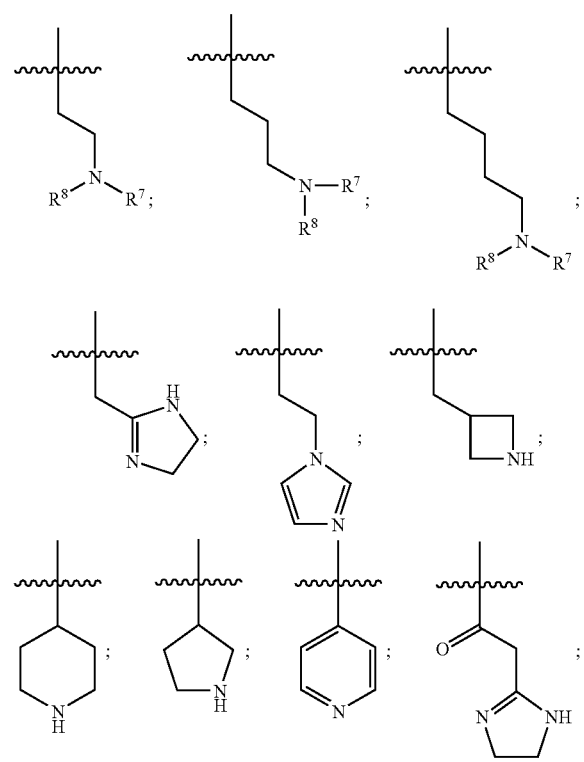

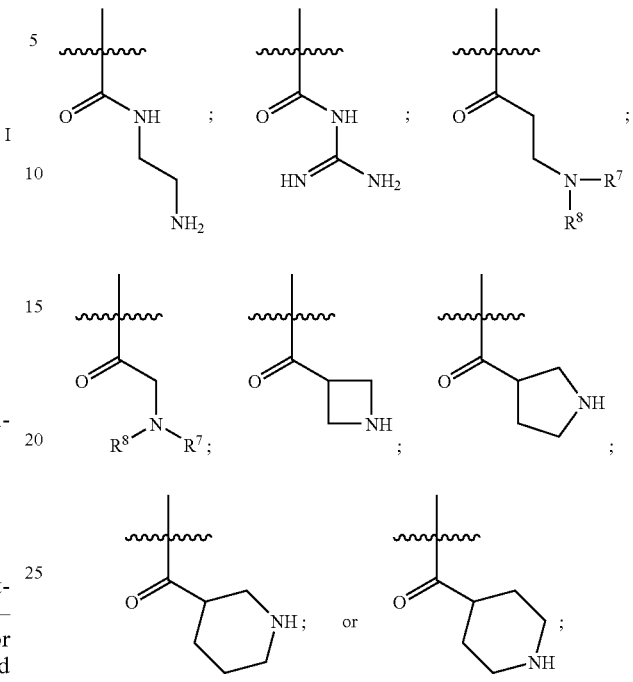

and
R$^7$ and R$^8$ each independently is hydrogen or alkyl.

2. The compound of claim 1, wherein R$^2$ and R$^3$ are hydrogen.

3. The compound of claim 1, wherein X is —CR$_2$—.

4. The compound of claim 1, wherein Ar is optionally substituted phenyl.

5. A pharmaceutical composition comprising an effective amount of the compound of claim 1 in admixture with a pharmaceutically acceptable carrier.

6. A method for treating a food uptake disorder, said method comprising administering to a subject in need thereof a therapeutically effective amount of a compound of claim 1.

7. The compound of claim 1, wherein Ar is phenyl optionally substituted from one to four times with a group independently selected from halo, alkyl, haloalkyl, heteroalkyl, alkoxy, cyano, S(O)$_s$—R$^j$, —C(=O)—NR$^k$R$^m$, SO$_2$—NR$^k$R$^m$, —N(R$^n$)—C(=O)—R$^p$, or —C(=O)—R$^p$, where s is from 0 to 2, R$^j$, R$^k$, R$^m$ and R$^n$ each independently is hydrogen or alkyl, and R$^p$ is hydrogen, alkyl, alkoxy or hydroxy.

8. The compound of claim 1, wherein R$^4$ is:

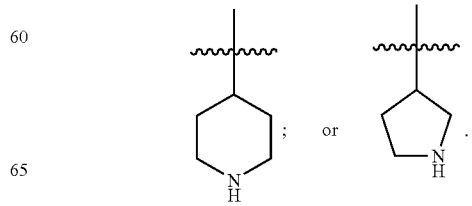

9. The compound of claim 8, wherein $R^4$ is:

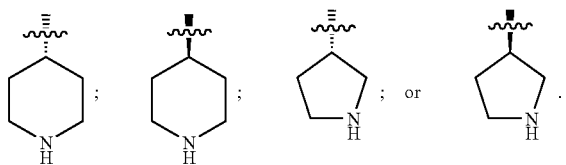

10. The compound of claim 1, wherein $R^2$ and $R^3$ are alkyl.

11. The compound of claim 1, wherein one of $R^2$ and $R^3$ is hydrogen and the other is alkyl.

12. A compound of selected from the group consisting of:
7-Benzenesulfonyl-4-(2-dimethylamino-ethyl)-4-benzo[1,4]oxazin-3-one;
7-Benzenesulfonyl-4-(3-dimethylamino-propyl)-4H-benzo[1,4]-oxazin-3-one;
4-(2-Amino-ethyl)-7-benzenesulfonyl-4H-benzo[1,4]oxazin-3-one;
7-Benzenesulfonyl-4-(4-dimethylamino-butyl)-4H-benzo[1,4]oxazin-3-one;
7-Benzenesulfonyl-4-(4,5-dihydro-1H-imidazol-2-ylmethyl)-4H-benzo[1,4]oxazin-3-one;
6-Benzenesulfonyl-4-(2-dimethylamino-ethyl)-4H-benzo[1,4]oxazin-3-one;
6-Benzenesulfonyl-4-(4,5-dihydro-1H-imidazol-2-ylmethyl)-4H-benzo[1,4]oxazin-3-one;
2-(6-Benzenesulfonyl-2,3-dihydro-benzo[1,4]oxazin-4-yl)-ethylamine;
1-(6-Benzenesulfonyl-2,3-dihydro-benzo[1,4]oxazin-4-yl)-2-(4,5-dihydro-1H-imidazol-2-yl)-ethanone;
6-Benzenesulfonyl-4-(4,5-dihydro-1H-imidazol-2-ylmethyl)-3,4-dihydro-2H-benzo[1,4]oxazine;
N-(6-Benzenesulfonyl-2,3-dihydro-benzo[1,4]oxazine-4-carbonyl)-guanidine;
6-Benzenesulfonyl-2,3-dihydro-benzo[1,4]oxazine-4-carboxylic acid (2-amino-ethyl)-amide;
6-Benzenesulfonyl-4-piperidin-4-yl-3,4-dihydro-2H-benzo[1,4]oxazine;
1-(6-Benzenesulfonyl-2,3-dihydro-benzo[1,4]oxazin-4-yl)-3-dimethylamino-propan-1-one;
1-(6-Benzenesulfonyl-2,3-dihydro-benzo[1,4]oxazin-4-yl)-3-methylamino-propan-1-one;
1-(6-Benzenesulfonyl-2,3-dihydro-benzo[1,4]oxazin-4-yl)-2-methylamino-ethanone;
[3-(6-Benzenesulfonyl-2,3-dihydro-benzo[1,4]oxazin-4-yl)-propyl]-methyl-amine;
1-(6-Benzenesulfonyl-2,3-dihydro-benzo[1,4]oxazin-4-yl)-2-dimethylamino-ethanone;
7-Benzenesulfonyl-2,3-dihydro-benzo[1,4]oxazine-4-carboxylic acid (2-amino-ethyl)-amide;
1-(7-Benzenesulfonyl-2,3-dihydro-benzo[1,4]oxazin-4-yl)-2-(4,5-dihydro-1H-imidazol-2-yl)-ethanone;
N-(7-Benzenesulfonyl-2,3-dihydro-benzo[1,4]oxazine-4-carbonyl)-guanidine;
7-Benzenesulfonyl-4-piperidin-4-yl-3,4-dihydro-2H-benzo[1,4]oxazine;
2-(7-Benzenesulfonyl-2,3-dihydro-benzo[1,4]oxazin-4-yl)-ethylamine;
1-(7-Benzenesulfonyl-2,3-dihydro-benzo[1,4]oxazin-4-yl)-2-methylamino-ethanone;
1-(7-Benzenesulfonyl-2,3-dihydro-benzo[1,4]oxazin-4-yl)-3-methylamino-propan-1-one;
[3-(7-Benzenesulfonyl-2,3-dihydro-benzo[1,4]oxazin-4-yl)propyl]-methyl-amine;
7-Benzenesulfonyl-4-(2-imidazol-1-yl-ethyl)-3,4-dihydro-2H-benzo[1,4]oxazine;
Azetidin-3-yl-(7-benzenesulfonyl-2,3-dihydro-benzo[1,4]oxazin-4-yl)-methanone;
4-Azetidin-3-ylmethyl-7-benzenesulfonyl-3,4-dihydro-2H-benzo[1,4]oxazine;
(7-Benzenesulfonyl-2,3-dihydro-benzo[1,4]oxazin-4-yl)-pyrrolidin-3-yl-methanone;
(7-Benzenesulfonyl-2,3-dihydro-benzo[1,4]oxazin-4-yl)-piperidin-3-yl-methanone;
(7-Benzenesulfonyl-2,3-dihydro-benzo[1,4]oxazin-4-yl)-piperidin-4-yl-methanone;
7-Benzenesulfonyl-4-pyrrolidin-3-yl-3,4-dihydro-2H-benzo[1,4]oxazine;
7-Benzenesulfonyl-2,2-dimethyl-4-pyridin-4-yl-3,4-dihydro-2H-benzo[1,4]oxazine;
7-Benzenesulfonyl-2,2-dimethyl-4-piperidin-4-yl-3,4-dihydro-2H-benzo[1,4]oxazine;
7-Benzenesulfonyl-2,2-dimethyl-4-(1-methyl-piperidin-4-yl)-3,4-dihydro-2H-benzo[1,4]oxazine;
(R)-7-Benzenesulfonyl-4-pyrrolidin-3-yl-3,4-dihydro-2H-benzo[1,4]oxazine; and
(S)-7-Benzenesulfonyl-4-pyrrolidin-3-yl-3,4-dihydro-2H-benzo[1,4]oxazine.

13. A compound of formula VIIa or VIIb

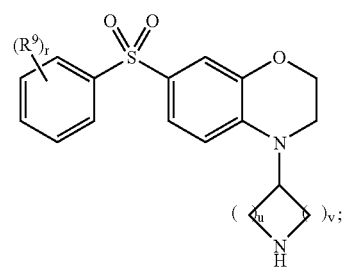

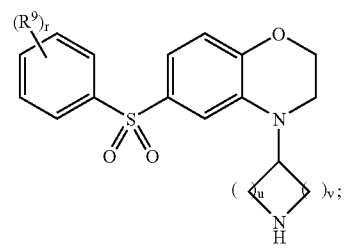

or a pharmaceutically acceptable salt thereof, wherein:
r is from 0 to 4;
u and v each independently is 1 or 2; and
each $R^9$ is independently halo, alkyl, haloalkyl, heteroalkyl, alkoxy, cyano, $-S(O)_s-R^j$, $-C(=O)-NR^kR^m$, $-SO_2-NR^kR^m$, $-N(R^n)-C(=O)-R^p$, or $-C(=O)-R^p$, where s is from 0 to 2, $R^j$, $R^k$, $R^m$ and $R^n$ each independently is hydrogen or alkyl, and $R^p$ is hydrogen, alkyl, alkoxy or hydroxy.

14. The compound of claim 13, wherein r is 0.

15. The compound of claim 13, wherein r is 0 or 1 and $R^9$ is halo, alkyl, alkoxy or haloalkyl.

16. The compound of claim 13, wherein u is 1 and v is 2.

17. The compound of claim 13, wherein u is 2 and v is 2.

* * * * *